United States Patent
Harran et al.

(10) Patent No.: US 10,040,780 B2
(45) Date of Patent: Aug. 7, 2018

(54) MCL-1 ANTAGONISTS

(71) Applicants: The Regents of the University of California, Oakland (CA); The Royal Institution for the Advancement of Learning/McGill University, Montreal (CA)

(72) Inventors: Patrick Harran, Santa Monica, CA (US); James H. Frederich, Manhattan Beach, CA (US); Gordon Shore, Montreal (CA); Mai Nguyen, Montreal (CA)

(73) Assignees: The Regents of the University of California, Oakland, CA (US); The Royal Institute for the Advancement of Learning/McGill University, Montreal (CA)

( * ) Notice: Subject to any disclaimer, the term of this patent is extended or adjusted under 35 U.S.C. 154(b) by 0 days.

(21) Appl. No.: 15/123,232

(22) PCT Filed: Mar. 3, 2015

(86) PCT No.: PCT/US2015/018540
§ 371 (c)(1),
(2) Date: Sep. 1, 2016

(87) PCT Pub. No.: WO2015/134539
PCT Pub. Date: Sep. 11, 2015

(65) Prior Publication Data
US 2017/0066747 A1 Mar. 9, 2017

Related U.S. Application Data

(60) Provisional application No. 61/947,211, filed on Mar. 3, 2014.

(51) Int. Cl.
C07D 405/04 (2006.01)
C07D 401/04 (2006.01)
C07D 405/12 (2006.01)
C07D 413/04 (2006.01)
C07D 471/04 (2006.01)
C07D 405/14 (2006.01)

(52) U.S. Cl.
CPC ......... *C07D 405/04* (2013.01); *C07D 401/04* (2013.01); *C07D 405/12* (2013.01); *C07D 405/14* (2013.01); *C07D 413/04* (2013.01); *C07D 471/04* (2013.01)

(58) Field of Classification Search
CPC .............................. C07D 405/04; C07D 401/04
See application file for complete search history.

(56) References Cited

U.S. PATENT DOCUMENTS

| 5,321,041 A | 6/1994 | Adachi et al. |
| 5,480,902 A * | 1/1996 | Addor ............... A01N 43/36 514/326 |
| 7,507,740 B2 * | 3/2009 | Ishikawa ............ C07D 487/16 514/265.1 |
| 2003/0119894 A1 | 6/2003 | Murthy et al. |

OTHER PUBLICATIONS

Becker et al (2003): STN International, HCAPLUS database (Columbus, Ohio),Accession No. 2003: 173091.*
Su et al (2012): STN International, HCAPLUS database (Columbus, Ohio), Accession No. 2012:1550840.*
Ishikawa et al (2005): STN International, HCAPLUS database (Columbus, Ohio),Accession No. 2005: 1314844.*
Addor et al (1996): STN International, HCAPLUS database (Columbus, Ohio), Accession No. 1996: 209990.*
Beroukhim, R. et al. (Feb. 18, 2010). "The landscape of somatic copy-number alteration across human cancers," *Nature* 463(7283):899-905.
Brumati, G. et al. (Nov. 2013). "Seeking a MCL-1 inhibitor," *Cell Death Differ* 20(11):1440-1441.
Cotter, T.G. (Jul. 2009). "Apoptosis and cancer: the genesis of a research field," Nat Rev Cancer 9(7):501-507.
Dalafave, D.S. et al. (Aug. 12, 2010). "Inhibition of Antiapoptotic BCL-XL, BCL-2, and MCL-1 Proteins by Small Molecule Mimetics," *Cancer Inform* 9:169-177.
Frederich, J.H. et al. (Mar. 13, 2013, e-published Mar. 1, 2013). "Modular access to complex prodiginines: total synthesis of (+)-roseophilin via its 2-azafulvene prototropisomer," *J Am Chem Soc* 135(10):3788-3791.
Friberg, A. et al. (Jan. 10, 2013, e-published Dec. 17, 2012). "Discovery of potent myeloid cell leukemia 1 (Mcl-1) inhibitors using fragment-based methods and structure-based design," *J Med Chem* 56(1):15-30.
International Search Report dated Jun. 10, 2015, for PCT Application No. PCT/US2015/018540, filed Mar. 3, 2015, 4 pages.
Konopleva, M. et al. (Aug. 2002). "The anti-apoptotic genes Bcl-X(L) and Bcl-2 are over-expressed and contribute to chemoresistance of non-proliferating leukaemic CD34+ cells," *Br J Haematol* 118(2):521-534.
Konopleva, M. et al. (Nov. 2006). "Mechanisms of apoptosis sensitivity and resistance to the BH3 mimetic ABT-737 in acute myeloid leukemia," *Cancer Cell* 10(5):375-388.
Lessene, G. et al (Dec. 2008). "BCL-2 family antagonists for cancer therapy," *Nat Rev Drug Discov* 7(12):989-1000.
Nguyen, M. et al. (Dec. 4, 2007, e-published Nov. 26, 2007). "Small molecule obatoclax (GX15-070) antagonizes MCL-1 and overcomes MCL-1-mediated resistance to apoptosis," *Proc Natl Acad Sci USA* 104(49):19512-19517.
Parkins, A.W. (Oct. 1996). "Catalytic Hydration of Nitriles to Amides," *Platinum Metals Review* 40(4):169-174.
Schimmer, A.D. et al. (Dec. 15, 2008). "A phase I study of the pan bcl-2 family inhibitor obatoclax mesylate in patients with advanced hematologic malignancies," *Clin Cancer Res* 14(24):8295-8301.

(Continued)

*Primary Examiner* — Golam M Shameem
(74) *Attorney, Agent, or Firm* — Mintz Levin Cohn Ferris Glovsky and Popeo, P.C.

(57) ABSTRACT

Provided herein are Mcl-1 antagonist compositions and methods of treating g the compositions described herein.

34 Claims, 11 Drawing Sheets

(56) References Cited

OTHER PUBLICATIONS

Van Delft, M.F. et al. (Nov. 2006). "The BH3 mimetic ABT-737 targets selective Bcl-2 proteins and efficiently induces apoptosis via Bak/Bax if Mcl-1 is neutralized," *Cancer Cell* 10(5);389-399.
Varadarajan, S. et al. (Nov. 2013, e-published Jul. 5, 2013). "Evaluation and critical assessment of putative MCL-1 inhibitors," *Cell Death Differ* 20(11):1475-1484.
Vogler, M. et al. (Jul. 2009, e-published Apr. 24, 2009). "Different forms of cell death induced by putative BCL2 inhibitors," *Cell Death Differ* 16(7):1030-1039.
Written Opinion dated Jun. 10, 2015, for PCT Application No. PCT/US2015/018540, filed Mar. 3, 2015, 5 pages.

\* cited by examiner

MCL-1 ANTAGONISTS

CROSS-REFERENCES TO RELATED APPLICATIONS

This application is a national stage aplication filed under 35 U.S.C. § 371, of International Patent Appl. No. PCT/US2015/018540, filed Mar. 3, 2015, which claims priority to U.S. Provisional Appl. No. 61/947,211, filed Mar. 3, 2014, which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48539-507001WO_ST25.TXT, created on Mar. 2, 2015, 761 bytes, machine format IBM-PC, MS-Windows operating system, is hereby incorporated by reference.

BACKGROUND OF THE INVENTION

Apoptosis is the biochemical program Applicants' bodies utilize to remove unwanted, damaged, or diseased cells. Deregulation of this process is required for cancer development and serves as a major barrier to effective treatment. Recent evidence suggests that one or more components of apoptotic signaling are disrupted in all human cancers, either by genetic mutation of genes encoding core apoptotic machinery or by other mechanisms (e.g. epigenetic mechanisms or upstream oncogenic mutations). These genetic changes provide cancer cells with a survival advantage, ensuring their uncontrolled growth. Despite the important role of apoptosis in the development and maintenance of cancer, few therapeutics targeting apoptotic signaling have reached clinical evaluation. The compositions and methods provided address these and other needs in the art.

BRIEF SUMMARY OF THE INVENTION

Provided herein are compounds having the formula:

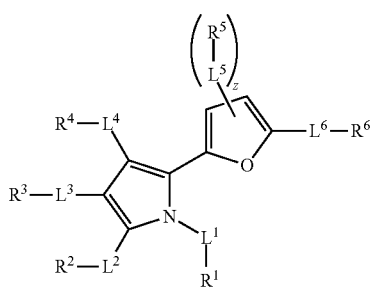

(I)

In the compound of formula (I), $L^1$, $L^2$, $L^3$, $L^4$, $L^5$, and $L^6$ are independently a bond, —CO— (i.e. —C(O)—), —COO— (i.e. —C(O)O—), —OCO— (i.e. —OC(O)—), —CONR$^7$— (i.e. —C(O)N(R$^7$)—), —NR$^7$CO— (i.e. —N(R$^7$)C(O)—), —O—, —SO$_n$— (i.e. —S(O)$_n$—), —SONR$^7$— (i.e. —S(O)N(R$^7$)—), —NR$^7$SO— (i.e. —N(R$^7$)S(O)—), —CONR$^7$SO$_2$— (i.e. —C(O)NR$^7$S(O)$_2$—), —SO$_2$NR$^7$CO— (i.e. —S(O)$_2$N(R$^7$)C(O)—), —NR$^7$— (i.e. —N(R$^7$)—), substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^7$ is independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_2$Ph, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n is 0, 1, or 2. $R^1$ is hydrogen, halogen, —N$_3$, —CF$_3$, —CCl$_3$, —CBr$_3$, —CI$_3$, —CN, —CHO, =O, —OR$^{1A}$, —NR$^{1B}$R$^{1C}$, —COR$^{1A}$, —COOR$^{1A}$, —CONR$^{1B}$R$^{1C}$, —NR$^{1B}$COR$^{1A}$, —NO$_2$, —SR$^{1D}$, —SO$_{n1}$R$^{1B}$, —S(O)$_{n1}$OR$^{1B}$, —S(O)$_{n1}$NR$^{1B}$R$^{1C}$, —NR$^{1B}$S(O)$_{n1}$R$^{1C}$, —NHNR$^{1B}$R$^{1C}$, —NHC(O)NHNR$^{1B}$R$^{1C}$, —NHC(O)NR$^{1B}$R$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^1$ and $R^2$ are optionally joined together to form a substituted or unsubstituted cycloalkyl, substituted or unsubstituted heterocycloalkyl, substituted or unsubstituted aryl, or substituted or unsubstituted heteroaryl. $R^2$ is hydrogen, halogen, —N$_3$, —CF$_3$, —CCl$_3$, —CBr$_3$, —CI$_3$, —CN, —CHO, =O, —OR$^{2A}$, —NR$^{2B}$R$^{2C}$, —COR$^{2A}$, —COOR$^{2A}$, —CONR$^{2B}$R$^{2C}$, —NR$^{2B}$COR$^{2A}$, —NO$_2$, —SR$^{2D}$, —SO$_{n2}$R$^{2B}$, —S(O)$_{n2}$OR$^{2B}$, —S(O)$_{n2}$NR$^{2B}$R$^{2C}$, —NR$^{2B}$S(O)$_{n2}$R$^{2C}$, —NHNR$^{2B}$R$^2$, —ONR$^{2B}$R$^2$, —NHC(O)NHNR$^{2B}$R$^{2C}$, —NHC(O)NR$^{2B}$R$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^2$ and $R^3$ are optionally joined together to form a substituted or unsubstituted cycloalkyl, substituted or unsubstituted heterocycloalkyl, substituted or unsubstituted aryl, or substituted or unsubstituted heteroaryl. $R^3$ is hydrogen, halogen, —N$_3$, —CF$_3$, —CCl$_3$, —CBr$_3$, —CI$_3$, —CN, —CHO, =O, —OR$^{3A}$, —NR$^{3B}$R$^{3C}$, —COR$^{3A}$, —COOR$^{3A}$, —CONR$^{3B}$R$^{3C}$, —NR$^{3B}$COR$^{3A}$, —NO$_2$, —SR$^{3D}$, —SO$_{n3}$R$^{3B}$, —S(O)$_{n3}$OR$^{3B}$, —S(O)$_{n3}$NR$^{3B}$R$^{3C}$, —NR$^{3B}$S(O)$_{n3}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^3$ and $R^4$ are optionally joined together to form a substituted or unsubstituted cycloalkyl, substituted or unsubstituted heterocycloalkyl, substituted or unsubstituted aryl, or substituted or unsubstituted heteroaryl. $R^4$ is hydrogen, halogen, —N$_3$, —CF$_3$, —CCl$_3$, —CBr$_3$, —CI$_3$, —CN, —CHO, =O, —OR$^{4A}$, —NR$^{4B}$R$^{4C}$, —COR$^{4A}$, —COOR$^{4A}$, —CONR$^{4B}$R$^{4C}$, —NR$^{4B}$COR$^{4A}$, —NO$_2$, —SR$^{4D}$, —SO$_{n4}$R$^{4B}$, —S(O)$_{n4}$OR$^{4B}$, —S(O)$_{n4}$NR$^{4B}$R$^{4C}$, —NR$^{4B}$S(O)$_{n4}$R$^{4C}$, —NHNR$^{4B}$R$^{4C}$, —ONR$^{4B}$R$^{4C}$, —NHC(O)NHNR$^{4B}$R$^{4C}$, —NHC(O)NR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently hydrogen, halogen, —N$_3$, —CF$_3$, —CCl$_3$, —CBr$_3$, —CI$_3$, —CN, —CHO, =O, —OR$^{5A}$, —NR$^{5B}$R$^{5C}$, —COR$^{5A}$, —COOR$^{5A}$, —CONR$^{5B}$R$^{8C}$, —NR$^{5B}$COR$^{5A}$, —$NO_2$, —$SR^{5D}$, —$SO_{n5}R^{5B}$, —$S(O)_{n5}OR^{5B}$, —$S(O)_{n5}NR^{5B}R^{5C}$, —$NR^{5B}S(O)_{n5}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^5$ and $R^6$ are optionally joined together to form a substituted or unsubstituted cycloalkyl, substituted or unsubstituted heterocycloalkyl, substituted or unsubstituted aryl, or substituted or unsubstituted heteroaryl. $R^6$ is hydrogen, halogen, —$N_3$, —$CF_3$, —$CCl_3$, —$CBr_3$, —$CI_3$, —CN, —CHO, =O, —$OR^{6A}$, —$NR^{6B}R^{6C}$, —$COR^{6A}$, —$COOR^{6A}$, —$CONR^{6B}R^{6C}$, —$NR^{6B}COR^{6A}$, —$NO_2$, —$SR^{6D}$, —$SO_{n6}R^{6B}$, —$S(O)_{n6}OR^{6B}$, —$S(O)_{n6}NR^{6B}R^{6C}$, —$NR^{6B}S(O)_{n6}R^{6C}$, —$NHNR^{6B}R^6$, —$ONR^{6B}R^6$, —$NHC(O)NHNR^{6B}R^{6C}$, —$NHC(O)NR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{2A}$, $R^{3A}$, $R^{4A}$, $R^{5A}$, $R^{6A}$, $R^{1B}$, $R^{2B}$, $R^{3B}$, $R^{4B}$, $R^{5B}$, $R^{6B}$, $R^{1C}$, $R^{2C}$, $R^{3C}$, $R^{4C}$, $R^{5C}$, $R^{6C}$, $R^{1D}$, $R^{2D}$, $R^{3D}$, $R^{4D}$, $R^{5D}$, and $R^{6D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{6B}$ and $R^{6C}$, are optionally joined together to form a substituted or unsubstituted cycloalkyl, substituted or unsubstituted heterocycloalkyl, substituted or unsubstituted aryl, or substituted or unsubstituted heteroaryl. The symbols n1, n2, n3, n4, n5, and n6 are independently 0, 1 or 2 (e.g. 1 or 2). The symbol z is 1 or 2.

Provided herein are pharmaceutical compositions that include a compound described herein (e.g. formula (I), (II), (III), (IV) or (V), including embodiments thereof) and a pharmaceutically acceptable excipient.

Also provided herein are methods of treating cancer in a subject in need thereof by administering an effective amount of a compound described herein (e.g. formula (I), (II), (III), (IV) or (V), including embodiments thereof) to the subject.

Provided herein are methods of antagonizing Mcl-1 by contacting an Mcl-1 (e.g. an Mcl-1 mixture) with a compound described herein (e.g. formula (I), (II), (III), (IV) or (V), including embodiments thereof).

BRIEF DESCRIPTION OF THE DRAWINGS

FIG. 2A (Left panel): Schematic depicting liposome functional assay for recapitulating mitochondrial membrane permeability. FIG. 2A (right panel): Time course of liposomal functional assay. FIG. 2B (left panel): Legend of compound structures; FIG. 2B (right panel): Histogram depicting percentage cell death as a function of concentration for compounds 8, 9 and 10.

FIG. 5A (left penal): Data for liposome functional assay. FIG. 5A (right panel): Time course of calcium release for recited compounds. FIG. 5B (left panel): Data for in vitro cytotoxicity assay. FIG. 5B (right panel): Histogram depicting percentage cell death as a function of concentration for recited compounds.

FIGS. 8A-8B: Binding of benzothiophene 7 to purified Mcl-1 was detectable by ITC ($K_D$=1.0±0.41 μM). This was not the case for derived primary alcohol 8. FIG. 8C. PyMOL rendering of compound 7 bound to Mcl-1 in the solid state (PDB:4HW3). FIG. 8D. Pyrrolofuran 5 could be docked (Autodock Vina) into the same space on Mcl-1 occupied by 7, wherein its carbonyl group is oriented proximal to R263, analogous to the carboxylate group in 7. See reference 18 of Example; 2.

DETAILED DESCRIPTION OF THE INVENTION

Definitions

Figure 1:
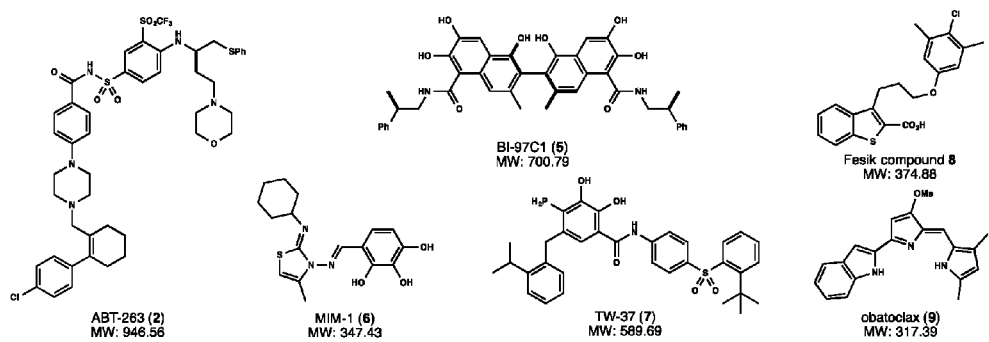
FIG. 1. Structures of putative Mcl-1 inhibitors reported in the literature.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded ("=O") to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$N(R)('R"—NRSO$_2$R'), —CN, and —$NO_2$ in a number ranging from zero to (2m'±1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", NR"C(O)$_2$R', NRC(NR'R")=NR'", S(O)R', —S(O)$_2$R', —S(O)$_2$N(R')(R", —NRSO$_2$R'), —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{14}$-substituted or unsubstituted alkyl, a plurality of $R^{14}$ substituents may be attached to the alkyl moiety wherein each $R^{14}$ substituent is optionally different. Where an R-substituted moiety is substituted with a plurality R substituents, each of the R-substituents may be differentiated herein using a prime symbol (') such as R', R", etc. For example, where a moiety is $R^{1A}$-substituted or unsubstituted alkyl, and the moiety is substituted with a plurality of $R^{1A}$ substituents, the plurality of $R^{1A}$ substituents may be differentiated as $R^{1A\prime}$, $R^{1A\prime\prime}$, $R^{1A\prime\prime\prime}$, etc. In some embodiments, the plurality of R substituents is 3. In some embodiments, the plurality of R substituents is 2.

In embodiments, a compound as described herein may include multiple instances of $R^1$, $R^2$, $R^3$, $R^4$, $R^5$, $R^6$, $R^{6A}$, $R^7$, and/or other substituents and variables. In such embodiments, each variable may optional be different and be appropriately labeled to distinguish each group for greater clarity. For example, where each $R^{6A}$ is different, they may be referred to, for example, as $R^{6A.1}$, $R^{6A.2}$, $R^{6A.3}$, or $R^{6A.4}$, respectively, wherein the definition of $R^{6A}$ is assumed by $R^{6A.1}$, $R^{6A.2}$, $R^{6A.3}$, and/or $R^{6A.4}$. The variables used within a definition of $R^1$, $R^2$, $R^3$, $R^4$, $R^5$, $R^6$, $R^{6A}$, $R^7$, and/or other variables that appear at multiple instances and are different may similarly be appropriately labeled to distinguish each group for greater clarity.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula —T—C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where variables s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "〜〜〜," denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms apply to macrocyclic peptides, peptides that have been modified with non-peptide functionality, peptidomimetics, polyamides, and macrolactams. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In embodiments, "treating" refers to treatment of cancer.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. infectious disease, hyperproliferative disease, cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with infection may be treated with an agent (e.g. compound as described herein) effective as an antibiotic.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

"Patient," "subject," "patient in need thereof," and "subject in need thereof" are herein used interchangeabley and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

In some embodiments, the disease is a disease having the symptom of cell hyperproliferation. In some embodiments, the disease is a disease having the symptom of an aberrant level of androgen receptor activity. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is prostate cancer. In embodiments, the disease is hormone sensitive prostate cancer. In embodiments, the disease is hormone refractory (insensitive) prostate cancer.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

"Mcl-1" is used according to its common, ordinary meaning and refers to proteins of the same or similar names and functional fragments and homologs thereof. The term includes recombinant or naturally occurring forms of Mcl-1 (e.g. Myeloid Leukemia sequence protein 1 (BCL2-related); GI No: 7582271, or variants thereof that maintain Mcl-1 activity (e.g. within at least 30%, 40%, 50%, 60%, 70%, 80%, 90%, 95%, or 100% activity compared to Mcl-1). A "Mcl-1 mixture" is a mixture that includes at least Mcl-1. Thus, in embodiments, a Mcl-1 mixture may be a region (e.g. cytoplasm, nucleus) within a cell. A Mcl-1 mixture may be a solution (e.g. a buffer or assay) which includes at least Mcl-1 and one other protein or receptor.

"Bcl-2" is used according to its common, ordinary meaning and refers to proteins of the same or similar names and functional fragments and homologs thereof. The term includes recombinant or naturally occurring forms of Bcl-2 (e.g. B cell lymphoma 2 protein); GI:72198189, or variants thereof that maintain Bcl-2 activity (e.g. within at least 30%, 40%, 50%, 60%, 70%, 80%, 90%, 95%, or 100% activity compared to Bcl-2). A "Bcl-2 mixture" is a mixture that includes at least Bcl-2. Thus, in embodiments, a Bcl-2 mixture may be a region (e.g. cytoplasm, nucleus) within a cell. A Bcl-2 mixture may be a solution (e.g. a buffer or assay) which includes at least Bcl-2 and one other protein or receptor.

"Bcl-xl" is used according to its common, ordinary meaning and refers to proteins of the same or similar names and functional fragments and homologs thereof. The term includes recombinant or naturally occurring forms of Bcl-xl (e.g. BCL2-like 1 isoform 1) or variants thereof that maintain Bcl-xl activity (e.g. within at least 30%, 40%, 50%, 60%, 70%, 80%, 90%, 95%, or 100% activity compared to Bcl-xl). A "Bcl-xl mixture" is a mixture that includes at least Bcl-xl. Thus, in embodiments, a Bcl-xl mixture may be a region (e.g. cytoplasm, nucleus) within a cell. A Bcl-xl mixture may be a solution (e.g. a buffer or assay) which includes at least Bcl-xl and one other protein or receptor.

The term "associated" or "associated with" in the context of a substance or substance activity or function associated with a disease means that the disease is caused by or otherwise characterized by (in whole or in part), a symptom of the disease is caused by (in whole or in part) the substance or substance activity or function, or a side-effect of the compound (e.g. toxicity) is caused by or characterized by (in whole or in part) the substance or substance activity or function.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

An "agonist," as used herein, refers to a compound capable of detectably increasing the expression or activity of a given protein or receptor. The agonist can increase expression or activity 10%, 20%, 30%, 40%, 50%, 60%, 70%, 80%, 90%, 100% or more in comparison to a control in the absence of the agonist. In embodiments, expression or activity is 1.5-fold, 2-fold, 3-fold, 4-fold, 5-fold, 10-fold or more higher than the expression or activity in the absence of the agonist. An "Mcl-1 agonist" is a compound which increases Mcl-1 activity. A Mcl-1 agonist may directly interact with Mcl-1 to increase its activity. Alternatively, a Mcl-1 agonist may increase and/or decrease the activity of a protein or receptor in a signaling pathway that is involved in the activation of Mcl-1 which increases Mcl-1 activity.

The term "antagonist" refers to a substance capable of detectably lowering expression or activity of a given protein relative to the absence of the antogonist. The antagonist can inhibit expression or activity 10%, 20%, 30%, 40%, 50%, 60%, 70%, 80%, 90%, 100% or less in comparison to a control in the absence of the antagonist. In embodiments, the inhibition is 1.5-fold, 2-fold, 3-fold, 4-fold, 5-fold, 10-fold, or more than the expression or activity in the absence of the antagonist. An "Mcl-1 antagonist" is a compound which decreases Mcl-1 activity. A Mcl-1 antagonist may directly interact with Mcl-1 to decrease its activity. Alternatively, a Mcl-1 antagonist may increase and/or decrease the activity of a protein or receptor in a signaling pathway that is involved in the activation of Mcl-1 which decreases Mcl-1 activity.

Compositions

Provided herein are compounds having the formula:

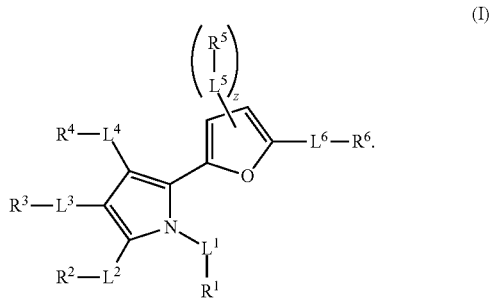

(I)

In embodiments, in the compound of formula (I), $L^1$, $L^2$, $L^3$, $L^4$, $L^5$, and $L^6$ are independently a bond, —C(O)—, —C(O)O—, —C(O)NR$^7$—, —O—, —S(O)$_n$—, —S(O)NR$^7$—, —C(O)NR$^7$S(O)$_2$—, —NR$^7$—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^7$ is independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_2$Ph, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n is 0, 1, or 2. $R^1$ is hydrogen, halogen, —N$_3$, —CF$_3$, —CCl$_3$, —CBr$_3$, —CI$_3$, —CN, —CHO, =O, —OR$^{1A}$, —NR$^{1B}$R$^{1C}$, —COOR$^{1A}$, —CONR$^{1B}$R$^{1C}$, —NO$_2$, —SR$^{1D}$, —SO$_{n1}$R$^{1B}$, —S(O)$_{n1}$OR$^{1B}$, —S(O)$_{n1}$NR$^{1B}$R$^{1C}$, —NHNR$^{1B}$R$^{1C}$, —ONR$^{1B}$R$^{1C}$, —NHC(O)NHNR$^{1B}$R$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^1$ and $R^2$ are optionally joined together to form a substituted or unsubstituted cycloalkyl, substituted or unsubstituted heterocycloalkyl, substituted or unsubstituted aryl, or substituted or unsubstituted heteroaryl. $R^2$ is independently hydrogen, halogen, —N$_3$, —CF$_3$, —CCl$_3$, —CBr$_3$, —CI$_3$, —CN, —CHO, =O, —OR$^{2A}$, —NR$^{2B}$R$^{2C}$, —COOR$^{2A}$, —CONR$^{2B}$R$^{2C}$, NO$_2$, SR$^{2D}$, —SO$_2$R$^{2B}$, —SO$_{n2}$OR$^{2B}$, —SO$_{n2}$NR$^{2B}$R$^{2C}$, —NHNR$^{2B}$R$^2$, —ONR$^{2B}$R$^{2C}$, —NHC(O)NHNR$^{2B}$R$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^2$ and $R^3$ are optionally joined together to form a substituted or unsubstituted cycloalkyl, substituted or unsubstituted heterocycloalkyl, substituted or unsubstituted aryl, or substituted or unsubstituted heteroaryl. $R^3$ is independently hydrogen, halogen, —N$_3$, —CF$_3$, —CCl$_3$, —CBr$_3$, —CI$_3$, —CN, —CHO, =O, —OR$^{3A}$, —NR$^{3B}$R$^{3C}$, —COOR$^{3A}$, —CONR$^{3B}$R$^{3C}$, NO$_2$, SR$^{3D}$, —SO$_{n3}$R$^{3B}$, —SO$_{n3}$OR$^{3B}$, —SO$_{n3}$NR$^{3B}$R$^{3C}$, —NHNR$^{3B}$R$^{3C}$, —ONR$^{3B}$R$^{3C}$, —NHC(O)NHNR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^3$ and $R^4$ are optionally joined together to form a substituted or unsubstituted cycloalkyl, substituted or unsubstituted heterocycloalkyl, substituted or unsubstituted aryl, or substituted or unsubstituted heteroaryl. $R^4$ is independently hydrogen, halogen, —N$_3$, —CF$_3$, —CCl$_3$, —CBr$_3$, —CI$_3$, —CN, —CHO, =O, —OR$^{4A}$, —NR$^{4B}$R$^{4C}$, —COOR$^{4A}$, —CONR$^{4B}$R$^{4C}$, NO$_2$, SR$^{4D}$, —SO$_{n4}$R$^{4B}$, —SO$_{n4}$OR$^{4B}$, —SO$_{n4}$NR$^{4B}$R$^{4C}$, —NHNR$^{4B}$R$^{4C}$, —ONR$^{4B}$R$^{4C}$, —NHC(O)NHNR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently hydrogen, halogen, —N$_3$, —CF$_3$, —CCl$_3$, —CBr$_3$, —CI$_3$, —CN, —CHO, =O, —OR$^{5A}$, —NR$^{5B}$R$^{1C}$, —COOR$^{5A}$, —CONR$^{5B}$R$^{5C}$, NO$_2$, SR$^{5D}$, —SO$_{n5}$R$^{5B}$, —SO$_{n5}$OR$^{5B}$, —SO$_{n5}$NR$^{5B}$R$^{5C}$, —NHNR$^{5B}$R$^{5C}$, —ONR$^{5B}$R$^{5C}$, —NHC(O)NHNR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^5$ and $R^6$ are optionally joined together to form a substituted or unsubstituted cycloalkyl, substituted or unsubstituted heterocycloalkyl, substituted or unsubstituted aryl, or substituted or unsubstituted heteroaryl. $R^6$ is independently hydrogen, halogen, $-N_3$, $-CF_3$, $-CCl_3$, $-CBr_3$, $-CI_3$, $-CN$, $-CHO$, $=O$, $-OR^{6A}$, $-NR^{6B}R^{6C}$, $-COOR^{6A}$, $-CONR^{6B}R^{6C}$, $NO_2$, $SR^{6D}$, $-SO_{n6}R^{6B}$, $-SO_{n6}OR^{6B}$, $-SO_{n6}NR^{6B}R^{6C}$, $-NHNR^{6B}R^6$, $-ONR^{6B}R^{6C}$, $-NHC(O)NHNR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{2A}$, $R^{3A}$, $R^{4A}$, $R^{5A}$, $R^{6A}$, $R^{1B}$, $R^{2B}$, $R^{3B}$, $R^{4B}$, $R^{5B}$, $R^{6B}$, $R^{1C}$, $R^{2C}$, $R^{3C}$, $R^{4C}$, $R^{5C}$, $R^{6C}$, $R^{1D}$, $R^{2D}$, $R^{3D}$, $R^{4D}$, $R^{5D}$, and $R^{6D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{6B}$ and $R^{6C}$, are optionally joined together to form a substituted or unsubstituted cycloalkyl, substituted or unsubstituted heterocycloalkyl, substituted or unsubstituted aryl, or substituted or unsubstituted heteroaryl. The symbols n1, n2, n3, n4, n5, and n6 are independently 1 or 2. The symbol z is 1 or 2. The symbol z may be 1. The symbol z may be 2. The symbols n1, n2, n3, n4, n5, and n6 may independently be 1. The symbols n1, n2, n3, n4, n5, and n6 may independently be 2.

In embodiments $L^1$ is a bond, $-S(O)_2-$, or substituted or unsubstituted alkylene. In embodiments, $L^1$ is a bond, $-S(O)_2-$. In embodiments, $L^1$ is substituted or unsubstituted $C_1$-$C_3$ alkylene. In embodiments, $L^1$ is unsubstituted $C_1$-$C_3$ alkylene.

In embodiments, $L^2$ and $L^3$ are independently a bond or substituted or unsubstituted alkylene. In embodiments, $L^2$ and $L^3$ are a bond. In embodiments, $L^2$ and $L^3$ are independently substituted or unsubstituted $C_1$-$C_3$ alkylene. In embodiments, $L^2$ and $L^3$ are independently unsubstituted $C_1$-$C_3$ alkylene.

In embodiments, $L^4$ is a bond, $S(O)_2-$, or substituted or unsubstituted alkylene. In embodiments, $L^4$ is a bond or $S(O)_2-$. In embodiments, $L^4$ is substituted or unsubstituted $C_1$-$C_3$ alkylene. In embodiments, $L^4$ is unsubstituted $C_1$-$C_3$ alkylene.

In embodiments, $L^5$ is a bond, $-O-$, or substituted or unsubstituted alkylene. In embodiments, $L^5$ is substituted or unsubstituted $C_1$-$C_3$ alkylene. In embodiments, $L^5$ is a bond. In embodiments, $L^5$ is $-O-$.

In embodiments, $L^6$ includes a salt bridge forming moiety. A salt bridge forming moiety as provided herein refers to a moiety capable of forming noncovalent interactions (e.g., hydrogen bonding, electrostatic interactions or a combination thereof) with other molecules. In embodiments, the salt bridge forming moiety is or includes $-NH_3^+$ or $-C(O)O^-$. In embodiments, the salt bridge moiety interacts with Arg 263 of Mcl-1 or a corresponding residue thereof. In embodiments, the salt bridge moiety does not bind to Bcl-2. In embodiments, the salt bridge moiety does not bind to Bcl-xl. In embodiments, the salt bridge moiety binds more specific to Mcl-1 than to Bcl-2 or Bcl-xl. In embodiments, the salt bridge moiety binds about 5 times more specific to Mcl-1 than to Bcl-2 or Bcl-xl. In embodiments, the salt bridge moiety binds about 10 times more specific to Mcl-1 than to Bcl-2 or Bcl-xl. In embodiments, the salt bridge moiety binds about 20 times more specific to Mcl-1 than to Bcl-2 or Bcl-xl. In embodiments, the salt bridge moiety binds about 30 times more specific to Mcl-1 than to Bcl-2 or Bcl-xl. In embodiments, the salt bridge moiety binds about 40 times more specific to Mcl-1 than to Bcl-2 or Bcl-xl. In embodiments, the salt bridge moiety binds about 50 times more specific to Mcl-1 than to Bcl-2 or Bcl-xl. In embodiments, the salt bridge moiety binds about 60 times more specific to Mcl-1 than to Bcl-2 or Bcl-xl. In embodiments, the salt bridge moiety binds about 70 times more specific to Mcl-1 than to Bcl-2 or Bcl-xl. In embodiments, the salt bridge moiety binds about 80 times more specific to Mcl-1 than to Bcl-2 or Bcl-xl. In embodiments, the salt bridge moiety binds about 90 times more specific to Mcl-1 than to Bcl-2 or Bcl-xl. In embodiments, the salt bridge moiety binds about 100 times more specific to Mcl-1 than to Bcl-2 or Bcl-xl. In embodiments, the salt bridge moiety binds about 200 times more specific to Mcl-1 than to Bcl-2 or Bcl-xl. In embodiments, the salt bridge moiety binds about 300 times more specific to Mcl-1 than to Bcl-2 or Bcl-xl. In embodiments, the salt bridge moiety binds about 400 times more specific to Mcl-1 than to Bcl-2 or Bcl-xl. In embodiments, the salt bridge moiety binds about 500 times more specific to Mcl-1 than to Bcl-2 or Bcl-xl. In embodiments, the salt bridge moiety binds about 1000 times more specific to Mcl-1 than to Bcl-2 or Bcl-xl.

In embodiments, the salt bridge moiety binds more specifically to Mcl-1 than to Bcl-2 or Bcl-xl. In embodiments, the salt bridge moiety binds at least 2 times more specific to Mcl-1 than to Bcl-2 or Bcl-xl. In embodiments, the salt bridge moiety binds at least 5 times more specific to Mcl-1 than to Bcl-2 or Bcl-xl. In embodiments, the salt bridge moiety binds at least 10 times more specific to Mcl-1 than to Bcl-2 or Bcl-xl. In embodiments, the salt bridge moiety binds at least 20 times more specific to Mcl-1 than to Bcl-2 or Bcl-xl. In embodiments, the salt bridge moiety binds at least 30 times more specific to Mcl-1 than to Bcl-2 or Bcl-xl. In embodiments, the salt bridge moiety binds at least 40 times more specific to Mcl-1 than to Bcl-2 or Bcl-xl. In embodiments, the salt bridge moiety binds at least 50 times more specific to Mcl-1 than to Bcl-2 or Bcl-xl. In embodiments, the salt bridge moiety binds at least 60 times more specific to Mcl-1 than to Bcl-2 or Bcl-xl. In embodiments, the salt bridge moiety binds at least 70 times more specific to Mcl-1 than to Bcl-2 or Bcl-xl. In embodiments, the salt bridge moiety binds at least 80 times more specific to Mcl-1 than to Bcl-2 or Bcl-xl. In embodiments, the salt bridge moiety binds at least 90 times more specific to Mcl-1 than to Bcl-2 or Bcl-xl. In embodiments, the salt bridge moiety binds at least 100 times more specific to Mcl-1 than to Bcl-2 or Bcl-xl. In embodiments, the salt bridge moiety binds at least 200 times more specific to Mcl-1 than to Bcl-2 or Bcl-xl. In embodiments, the salt bridge moiety binds at least 300 times more specific to Mcl-1 than to Bcl-2 or Bcl-xl. In embodiments, the salt bridge moiety binds at least 400 times more specific to Mcl-1 than to Bcl-2 or Bcl-xl. In embodiments, the salt bridge moiety binds at least 500 times more specific to Mcl-1 than to Bcl-2 or Bcl-xl. In embodiments, the salt bridge moiety binds at least 1000 times more specific to Mcl-1 than to Bcl-2 or Bcl-xl. In embodiments, the salt bridge moiety binds at least 5, 10, 50, 100, 500 or 1000 times more specific to Mcl-1 than to Bcl-2 or Bcl-xl. Thus, in embodiments the compounds provided herein including embodiments thereof (e.g., compounds of formula (I), (II), (III), (IV), (IVA), (V) and (VA)) bind at least 5, 10, 50, 100, 500 or 1000 times more specific to Mcl-1 than to Bcl-2 or Bcl-xl. Where a compound provided herein binds "at least" 5 times more specific to Mcl-1 than to Bcl-2 or Bcl-xl, the dissociation constant (Kd) of the compound bound to Mcl-1 is 5 times less than the Kd of the same compound bound to Bcl-2 or Bcl-xl.

In embodiments, $L^6$ is a bond, —C(O)—, —C(O)NR$^7$, —S(O)$_2$—, —C(O)NR$^7$S(O)$_2$—, or substituted or unsubstituted alkylene. In embodiments, $L^6$ is a bond or —C(O)—. In embodiments, $L^6$ is —C(O)NR$^7$S(O)$_2$— and $R^7$ is hydrogen.

In embodiments, the compound of formula (I) has the formula:

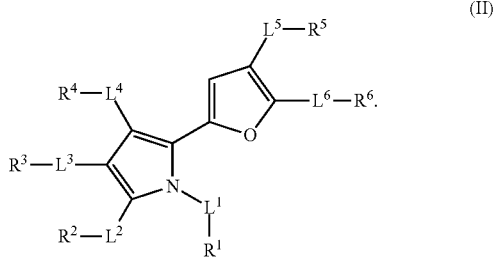

(II)

In embodiments, $R^1$ is a lipophilic substituent. A lipophilic substituent as provided herein is a substituent which increases the ability of a compound to dissolve in fats, oils, lipids, and non-polar solvents. In embodiments, the lipophilic substituent is a non-polar substituent. In embodiments, the lipophilic substituent is a large hydrocarbon moiety having the structure —(CH$_2$)$_{y1}$CH$_3$, wherein y1 is at least 1 (e.g. 1 to 100, 1-50, 1 to 20, 1 to 10). In embodiments, y1 is 1, 2, 3, 4, 5, 6, 7, 8, 9 or 10 In embodiments, $R^1$ is an aromatic lipophilic substituent. In embodiments, $R^1$ is substituted or unsubstituted alkyl, substituted or unsubstituted hetercycloalkyl, substituted or unsubstituted aryl, substituted or unsubstituted heteroaryl, or wherein $R^1$ and $R^2$ are joined together to form a substituted or unsubstituted heterocycloalkyl. In embodiments, $R^1$ is substituted or unsubstituted alkyl. In embodiments, $R^1$ is substituted or unsubstituted aryl or substituted or unsubstituted heteroaryl. In embodiments, $R^1$ and $R^2$ are joined together to form an R-substituted or unsubstituted heterocycloalkyl, wherein R is substituted or unsubstituted alkyl.

In embodiments, $R^1$ is hydrogen, halogen, —N$_3$, —CF$_3$, —CCl$_3$, —CBr$_3$, —CI$_3$, —CN, —CHO, =O, —OR$^{1A}$, —NR$^{1B}$R$^{1C}$, —COOR$^{1A}$, —CONR$^{1B}$R$^{1C}$, —NO$_2$, —SR$^{1D}$, —SO$_{n1}$R$^{1B}$, —S(O)$_{n1}$OR$^{1B}$, —S(O)$_{n1}$NR$^{1B}$R$^{1C}$, —NHNR$^{1B}$R$^{1C}$, —ONR$^{1B}$R$^{1C}$, —NHC(O)NHNR$^{1B}$R$^{1C}$, $R^9$-substituted or unsubstituted alkyl, $R^9$-substituted or unsubstituted heteroalkyl, $R^9$-substituted or unsubstituted cycloalkyl, substituted or unsubstituted heterocycloalkyl, $R^9$-substituted or unsubstituted aryl, or $R^9$-substituted or unsubstituted heteroaryl, wherein $R^1$ and $R^2$ are optionally joined together to form a $R^9$-substituted or unsubstituted cycloalkyl, $R^9$-substituted or unsubstituted heterocycloalkyl, $R^9$-substituted or unsubstituted aryl, or $R^9$-substituted or unsubstituted heteroaryl.

$R^9$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, $R^{10}$-substituted or unsubstituted alkyl, $R^{10}$-substituted or unsubstituted heteroalkyl, $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl.

$R^{10}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is independently hydrogen, halogen, —N$_3$, —CF$_3$, —CCl$_3$, —CBr$_3$, —CI$_3$, —CN, —CHO, =O, —OR$^{2A}$, —NR$^{2B}$R$^{2C}$, —COOR$^{2A}$, —CONR$^{2B}$R$^2$, NO$_2$, SR$^{2D}$, —SO$_{n2}$R$^{2B}$, —SO$_{n2}$OR$^{2B}$, —SO$_{n2}$NR$^{2B}$R$^{2C}$, —NHNR$^{2B}$R$^{2C}$, —ONR$^{2B}$R$^{2C}$, —NHC(O)NHNR$^{2B}$R$^{2C}$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl, wherein $R^2$ and $R^3$ are optionally joined together to form a $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

$R^{19}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

$R^{20}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^3$ is independently hydrogen, halogen, —N$_3$, —CF$_3$, —CCl$_3$, —CBr$_3$, —CI$_3$, —CN, —CHO, =O, —OR$^{3A}$, —NR$^{3B}$R$^{3C}$, —COOR$^{3A}$, —CONR$^{3B}$R$^{3C}$, NO$_2$, SR$^{3D}$, —SO$_{n3}$R$^{3B}$, —SO$_{n3}$R$^{3B}$, —SO$_{n3}$NR$^{3B}$R$^{3C}$, —NHNR$^{3B}$R$^{3C}$, —ONR$^{3B}$R$^{3C}$, —NHC(O)NHNR$^{3B}$R$^{3C}$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl, wherein $R^2$ and $R^3$ are optionally joined together to form a $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

$R^{21}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

$R^{22}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is hydrogen, joined together with $R^1$ to form a substituted or unsubstituted cycloalkyl, substituted or unsubstituted heterocycloalkyl, substituted or unsubstituted aryl, or substituted or unsubstituted heteroaryl. In embodiments, $R^2$ is hydrogen, joined together with $R^3$ to form a substituted or unsubstituted cycloalkyl, substituted or unsubstituted heterocycloalkyl, substituted or unsubstituted aryl, or substituted or unsubstituted heteroaryl. In embodiments, $R^2$ is hydrogen, joined together with $R^1$ to form a substituted or unsubstituted cycloalkyl or substituted or unsubstituted heterocycloalkyl, or joined together with $R^3$ to form substituted or unsubstituted heterocycloalkyl or substituted or unsubstituted aryl. In embodiments, $R^2$ is hydrogen. In embodiments, $R^2$ is not hydrogen. In embodiments, $R^2$ is joined together with $R^3$ to form a substituted or unsubstituted aryl. In embodiments, $R^2$ is joined together with $R^1$ to form a substituted or unsubstituted heterocycloalkyl.

In embodiments, $R^3$ is hydrogen. In embodiments, $R^2$ and $R^3$ are hydrogen.

In embodiments, the compound of formula (I) has the formula:

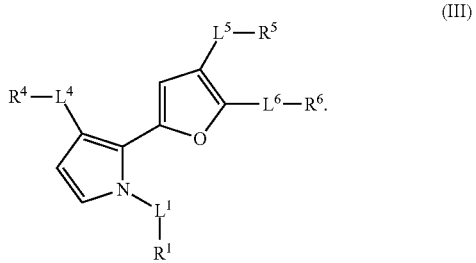

(III)

In embodiments, $R^4$ is halogen, substituted or substituted alkyl, substituted or unsubstituted heteroalkyl, substituted or unsubstituted aryl or joined together with $R^3$ to form a substituted or unsubstituted cycloalkyl, substituted or unsubstituted heterocycloalkyl, substituted or unsubstituted aryl or substituted or unsubstituted heteroaryl. In embodiments, $R^4$ is halogen. In embodiments, $R^4$ is $R^{11}$-substituted or unsubstituted alkyl. In embodiments, $R^4$ is $R^{11}$-substituted or unsubstituted aryl. In embodiments, $R^4$ and $R^3$ to form a substituted or unsubstituted cycloalkyl, substituted or unsubstituted heterocycloalkyl, or substituted or unsubstituted aryl.

In embodiments, $R^4$ is independently hydrogen, halogen, $-N_3$, $-CF_3$, $-CCl_3$, $-CBr_3$, $-CI_3$, $-CN$, $-CHO$, $=O$, $-OR^{4A}$, $-NR^{4B}R^{4C}$, $-COOR^{4A}$, $-CONR^{4B}R^{4C}$, $-NO_2$, $-SR^{4D}$, $-SO_{n4}R^{4B}$, $-SO_{n4}OR^{4B}$, $-SO_{n4}NR^{4B}R^{4C}$, $-NHNR^{4B}R^{4C}$, $-ONR^{4B}R^{4C}$, $-NHC(O)NHNR^{4B}R^{4C}$, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl.

$R^{11}$ is independently halogen, $-N_3$, $-NO_2$, $-CF_3$, $-CCl_3$, $-CBr_3$, $-CI_3$, $-CN$, $-OH$, $=O$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl.

$R^{12}$ is independently halogen, $-N_3$, $-NO_2$, $-CF_3$, $-CCl_3$, $-CBr_3$, $-CI_3$, $-CN$, $-OH$, $=O$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{11}$ is independently halogen, oxo, $-OH$, substituted or unsubstituted alkyl or substituted or unsubstituted aryl.

In embodiments, $R^5$ is independently $-OR^{5A}$, $CF_3$, substituted or unsubstituted alkyl, substituted or unsubstituted aryl, substituted or unsubstituted heteroaryl.

In embodiments, $R^5$ is independently $-OR^{5A}$, wherein $R^{5A}$ is $R^{13}$-substituted or unsubstituted alkyl, $R^{13}$-substituted or unsubstituted heteroalkyl, $R^{13}$ is halogen $-OH$, $=O$, $CF_3$, $-NR^{13A}R^{13B}$, substituted or unsubstituted alkyl, substituted or unsubstituted aryl, or substituted or unsubstituted heteroaryl, $R^{13A}$ and $R^{13B}$ are independently hydrogen or substituted or unsubstituted alkyl. In embodiments, $R^5$ is joined together with $R^6$ to form a substituted or unsubstituted heterocycloalkyl or substituted or unsubstituted heteroaryl.

In embodiments, $R^5$ is independently hydrogen, halogen, $-N_3$, $-CF_3$, $-CCl_3$, $-CBr_3$, $-CI_3$, $-CN$, $-CHO$, $-OR^{5A}$, $=O$, $-NR^{5B}R^{5C}$, $-COOR^{5A}$, $-CONR^{5B}R^{5C}$, $-NO_2$, $-SR^{5D}$, $-SO_{n5}R^{5B}$, $-SO_{n5}OR^{5B}$, $-SO_{n5}NR^{5B}R^{5C}$, $-NHNR^{5B}R^{5C}$, $-ONR^{5B}R^{5C}$, $-NHC(O)NHNR^{5B}R^{5C}$, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl, wherein $R^5$ and $R^6$ are optionally joined together to form a $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl.

$R^{13}$ is independently halogen, $-N_3$, $-NO_2$, $-CF_3$, $-CCl_3$, $-CBr_3$, $-CI_3$, $-CN$, $-OH$, $=O$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl.

$R^{13A}$ is independently halogen, $-N_3$, $-NO_2$, $-CF_3$, $-CCl_3$, $-CBr_3$, $-CI_3$, $-CN$, $-OH$, $=O$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{14A}$-substituted or unsubstituted alkyl, $R^{14A}$-substituted or unsubstituted heteroalkyl, $R^{14A}$-substituted or unsubstituted cycloalkyl, $R^{14A}$-substituted or unsubstituted heterocycloalkyl, $R^{14A}$-substituted or unsubstituted aryl, or $R^{14A}$-substituted or unsubstituted heteroaryl.

$R^{13B}$ is independently halogen, $-N_3$, $-NO_2$, $-CF_3$, $-CCl_3$, $-CBr_3$, $-CI_3$, $-CN$, $-OH$, $=O$, $-NH_2$, $-COOH$, $-CONH_2$, $-SH$, $-SO_3H$, $-SO_4H$, $-SO_2NH_2$, $-NHNH_2$, $-ONH_2$, $-OCH_3$, $-NHC(O)NHNH_2$, $R^{14B}$-substituted or unsubstituted alkyl, $R^{14B}$-substituted or unsubstituted heteroalkyl, $R^{14B}$-substituted or unsubstituted cycloalkyl, $R^{14B}$-substituted or unsubstituted heterocycloalkyl, $R^{14B}$-substituted or unsubstituted aryl, or $R^{14B}$-substituted or unsubstituted heteroaryl.

$R^{14}$ is independently halogen, $-N_3$, $-NO_2$, $-CF_3$, $-CCl_3$, $-CBr_3$, $-CI_3$, $-CN$, $-OH$, $=O$, $-NH_2$, $-COOH$, $-CONH_2$, $-SH$, $-SO_3H$, $-SO_4H$, —SO$_2$NH$_2$, —NHNH$_2$, —ONH$_2$, —OCH$_3$, —NHC(O)NHNH$_2$, R$^{15}$-substituted or unsubstituted alkyl, R$^{15}$-substituted or unsubstituted heteroalkyl, R$^{15}$-substituted or unsubstituted cycloalkyl, R$^{15}$-substituted or unsubstituted heterocycloalkyl, R$^{15}$-substituted or unsubstituted aryl, or R$^{15}$-substituted or unsubstituted heteroaryl.

R$^{14A}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{15}$-substituted or unsubstituted alkyl, R$^{15}$-substituted or unsubstituted heteroalkyl, R$^{15}$-substituted or unsubstituted cycloalkyl, R$^{15}$-substituted or unsubstituted heterocycloalkyl, R$^{15}$-substituted or unsubstituted aryl, or R$^{15}$-substituted or unsubstituted heteroaryl.

R$^{14B}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{15}$-substituted or unsubstituted alkyl, R$^{15}$-substituted or unsubstituted heteroalkyl, R$^{15}$-substituted or unsubstituted cycloalkyl, R$^{15}$-substituted or unsubstituted heterocycloalkyl, R$^{15}$-substituted or unsubstituted aryl, or R$^{15}$-substituted or unsubstituted heteroaryl.

R$^{15}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^6$ includes a salt bridge forming moiety. A salt bridge forming moiety as provided herein refers to a moiety capable of forming noncovalent interactions (e.g., hydrogen bonding, electrostatic interactions or a combination thereof) with other molecules. In embodiments, the salt bridge forming moiety is NH$_3$— or C(O)O—. In embodiments, the salt bridge moiety interacts with Arg 263 of Mcl-1 or a corresponding residue thereof. In embodiments, the salt bridge moiety does not interact with Bcl-2.

In embodiments, R$^6$ is independently halogen, —CN, substituted or unsubstituted alkyl, substituted or unsubstituted heterocycloalkyl, substituted or unsubstituted aryl, substituted or unsubstituted heteroaryl.

In embodiments, R$^6$ is independently hydrogen, halogen, —N$_3$, —CF$_3$, —CCl$_3$, —CBr$_3$, —CI$_3$, —CN, —CHO, =O, —OR$^{6A}$, —NR$^{6B}$R$^{6C}$, —COOR$^{6A}$, —CONR$^{6B}$R$^{6C}$, —NO$_2$, —SR$^{6D}$, —SO$_{n6}$R$^{6B}$, —SO$_{n6}$OR$^{6B}$, —SO$_{n6}$NR$^{6B}$R$^{6C}$, —NHNR$^{6B}$R$^6$, —ONR$^{6B}$R$^{6C}$, —NHC(O)NHNR$^{6B}$R$^{6C}$, R$^{16}$-substituted or unsubstituted alkyl, R$^{16}$-substituted or unsubstituted heteroalkyl, R$^{16}$-substituted or unsubstituted cycloalkyl, R$^{16}$-substituted or unsubstituted heterocycloalkyl, R$^{16}$-substituted or unsubstituted aryl, or R$^{16}$-substituted or unsubstituted heteroaryl.

R$^{16}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, NR$^{16A}$R$^{16B}$, R$^{17}$-substituted or unsubstituted alkyl, R$^{17}$-substituted or unsubstituted heteroalkyl, R$^{17}$-substituted or unsubstituted cycloalkyl, R$^{17}$-substituted or unsubstituted heterocycloalkyl, R$^{17}$-substituted or unsubstituted aryl, or R$^{17}$-substituted or unsubstituted heteroaryl.

R$^{16A}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{17A}$-substituted or unsubstituted alkyl, R$^{17A}$-substituted or unsubstituted heteroalkyl, R$^{17A}$-substituted or unsubstituted cycloalkyl, R$^{17A}$-substituted or unsubstituted heterocycloalkyl, R$^{17A}$-substituted or unsubstituted aryl, or R$^{17A}$-substituted or unsubstituted heteroaryl.

R$^{16B}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{17B}$-substituted or unsubstituted alkyl, R$^{17B}$-substituted or unsubstituted heteroalkyl, R$^{17B}$-substituted or unsubstituted cycloalkyl, R$^{17B}$-substituted or unsubstituted heterocycloalkyl, R$^{17B}$-substituted or unsubstituted aryl, or R$^{17B}$-substituted or unsubstituted heteroaryl.

R$^{17}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{18}$-substituted or unsubstituted alkyl, R$^{18}$-substituted or unsubstituted heteroalkyl, R$^{18}$-substituted or unsubstituted cycloalkyl, R$^{18}$-substituted or unsubstituted heterocycloalkyl, R$^{18}$-substituted or unsubstituted aryl, or R$^{18}$-substituted or unsubstituted heteroaryl.

In embodiments, R$^{17}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{17A}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{18}$-substituted or unsubstituted alkyl, R$^{18}$-substituted or unsubstituted heteroalkyl, R$^{18}$-substituted or unsubstituted cycloalkyl, R$^{18}$-substituted or unsubstituted heterocycloalkyl, R$^{18}$-substituted or unsubstituted aryl, or R$^{18}$-substituted or unsubstituted heteroaryl.

R$^{17B}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, R$^{18}$-substituted or unsubstituted alkyl, R$^{18}$-substituted or unsubstituted heteroalkyl, R$^{18}$-substituted or unsubstituted cycloalkyl, R$^{18}$-substituted or unsubstituted heterocycloalkyl, R$^{18}$-substituted or unsubstituted aryl, or R$^{18}$-substituted or unsubstituted heteroaryl.

R$^{18}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

Further to any compound with structure of Formulae (I), (II) or (III), in embodiments R$^6$ is R$^{16}$-substituted or unsubstituted alkyl, wherein R$^{16}$ is NR$^{16A}$R$^{16B}$, R$^7$-substituted or unsubstituted heterocycloalkyl, R$^{17}$-substituted or unsubstituted aryl, R$^{16A}$ and R$^{16B}$ are independently substituted or unsubstituted alkyl, joined together to form a heterocycloalkyl. R$^{17}$ is halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Further to any compound with structure of Formulae (I), (II) or (III), in embodiments R$^1$ is substituted or unsubstituted C$_1$-C$_{10}$ alkyl. In embodiments, R$^1$ is substituted or unsubstituted C$_1$-C$_5$ alkyl. In embodiments, R$^1$ is R$^9$-substituted C$_2$ alkyl and R$^9$ is methyl.

In embodiments, the compound of formula (I) has the formula:

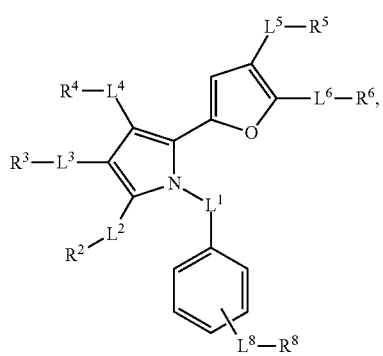

(IV)

Regarding Formula (IV), L$^8$ is independently a bond, —C(O)—, —C(O)O—, —OC(O)—, —C(O)NR$^7$—, —NR$^7$C(O)—, —O—, —S(O)$_{n9}$—, —S(O)NR$^7$—, —NR$^7$—, OR$^7$OP(O)—, NR$^7$S(O)$_2$—, —(NR$^7$)NP(O)—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene. The integer n9 is 0, 1 or 2 (e.g. 1 or 2). R$^8$ is independently hydrogen, halogen, —N$_3$, —CF$_3$, —CCl$_3$, —CBr$_3$, —CI$_3$, —CN, —CHO, =O, —OR$^{8A}$, —NR$^{8B}$R$^{8C}$, —COOR$^{8A}$, —CONR$^{8B}$R$^{8C}$, NO$_2$, SR$^{8D}$, —SO$_{n8}$R$^{8B}$, —SO$_{n8}$OR$^{8B}$, —SO$_{n8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{8A}$, R$^{8B}$, R$^{8C}$, and R$^{8D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n8 is 1, 2, 3, 4, or 5.

In embodiments, L$^1$ is a bond, —S(O)$_2$—, or substituted or unsubstituted C$_1$-C$_5$ alkylene.

In embodiments, L$^8$ is a bond or substituted or unsubstituted alkylene. In embodiments, L$^8$ is a bond or substituted or unsubstituted C$_1$-C$_5$ alkylene. In embodiments, R$^8$ is hydrogen, halogen or substituted or unsubstituted C$_1$-C$_5$ alkyl. In embodiments, R$^8$ is methyl.

In embodiments, the compound of formula (I) has the formula:

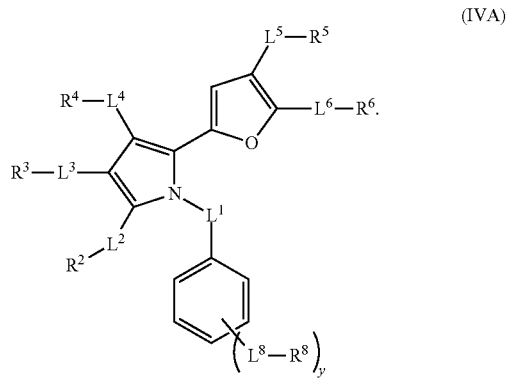

(IVA)

In formula (IVA) y is 1-5 and L$^1$, L$^2$, L$^3$, L$^4$, L$^5$, L$^6$, L$^8$, R$^2$, R$^3$, R$^4$, R$^5$, R$^6$ and R$^8$ are defined as described herein. In formula (IVA)-L$^8$-R$^8$ may occur more than once and be independently different. In embodiments, y is 1, 2, 3, 4 or 5.

In embodiments, L$^2$ and L$^3$ are independently a bond, or substituted or unsubstituted C$_1$-C$_5$ alkylene.

Further to any compound with structure of Formula (IV) or (IVA), in embodiments R$^2$ and R$^3$ are independently hydogen or are joined together to form a substituted or unsubstituted cycloalkyl, substituted or unsubstituted heterocycloalkyl, substituted or unsubstituted aryl or substituted or unsubstituted heteroaryl. In embodiments, wherein R$^2$ and R$^3$ are joined together to form an unsubstituted aryl. In embodiments, R$^2$ and R$^3$ are joined together to form an unsubstituted phenyl.

In embodiments, L$^4$ is a bond or substituted or unsubstituted C$_1$-C$_5$ alkylene.

In embodiments, R$^4$ is hydrogen, halogen or substituted or unsubstituted C$_1$-C$_5$ alkyl. In embodiments, R$^4$ is —Cl or —Br.

In embodiments, L$^5$ is a bond, —O—, substituted or unsubstituted C$_1$-C$_5$ alkylene or substituted or unsubstituted 1-5 membered heteroalkylene.

In embodiments, R$^5$ is hydrogen or substituted or unsubstituted C$_1$-C$_5$ alkyl. In embodiments, R$^5$ is unsubstituted C$_1$-C$_5$ alkyl. In embodiments, R$^5$ is methyl. In embodiments, R$^5$ is substituted C$_1$-C$_5$ alkyl. In embodiments, R$^5$ is R$^{13}$-substituted C$_1$-C$_3$ alkyl and R$^{13}$ is substituted or unsubstituted 6 membered heterocycloalkyl or substituted or unsubstituted 6 membered heteroaryl. In embodiments, R$^5$ is R$^{13}$-substituted C$_1$-C$_3$ alkyl and R$^{13}$ is unsubstituted morpholinyl or unsubstituted pyridinyl.

Further to any compound with structure of Formula (IV) or (IVA), in embodiments L$^6$ is a bond, —C(O)—, —C(O)O—, —C(O)NR$^7$S(O)$_2$—, or substituted or unsubstituted C$_1$-C$_5$ alkylene. In embodiments, R$^6$ is —C(O)OR$^{6A}$, substituted or unsubstituted C$_1$-C$_5$ alkyl, substituted or unsubstituted C$_1$-C$_5$ heteroalkyl, substituted or unsubstituted aryl, or substituted or unsubstituted heteroaryl. In embodiments, R$^6$ is —C(O)OR$^{6A}$ and R$^{6A}$ is hydrogen. In embodiments, R$^6$ is unsubstituted C$_1$-C$_3$ alkyl. In embodiments, R$^6$ is methyl. In embodiments, R$^6$ is substituted or unsubstituted C$_1$-C$_3$ alkyl. In embodiments, R$^6$ is R$^{16}$-substituted or unsubstituted C$_3$ alkyl and R$^{16}$ is substituted or unsubstituted 6 membered heterocycloalkyl. In embodiments, R$^6$ is R$^{16}$-substituted or unsubstituted C$_1$ alkyl and R$^{16}$ is substituted or unsubstituted aryl. In embodiments, R$^6$ is R$^{16}$-substituted C$_1$ alkyl, R$^{16}$ is R$^{17}$-substituted or unsubstituted phenyl and R$^{17}$ is —NH$_2$. In embodiments, R$^6$ is R$^{16}$-substituted or unsubstituted C$_1$ alkyl and R$^{16}$ is substituted or unsubstituted 6 membered heteroaryl. In embodiments, $R^6$ is $R^{16}$-substituted $C_1$ alkyl and $R^{16}$ is unsubstituted pyridinyl. In embodiments, $R^6$ is $R^{16}$-substituted $C_1$-$C_3$ heteroalkyl and $R^{16}$ is —O or —OH. In embodiments, $R^6$ is substituted or unsubstituted 5-8 membered aryl. In embodiments, $R^6$ is $R^{16}$-substituted or unsubstituted 5-6 membered aryl and $R^{16}$ is hydrogen, halogen, =O, —OH, or substituted or unsubstituted $C_1$-$C_5$ alkyl. In embodiments, $R^6$ is $R^{16}$-substituted or unsubstituted phenyl and $R^{16}$ is hydrogen, —OH, halogen or unsubstituted $C_1$-$C_3$ alkyl. In embodiments, $R^6$ is $R^{16}$-substituted or unsubstituted cyclopentadienyl and $R^{16}$ is —O or —OH. In embodiments, $R^6$ is substituted or unsubstituted 5-8 membered heteroaryl. In embodiments, $R^6$ is unsubstituted triazolyl, tetrazolyl, pyrrolyl, pyrridinyl or oxodiazolyl. In embodiments, $R^6$ is $R^{16}$-substituted 5-8 membered heteroaryl, $R^{16}$ is $R^{17}$-substituted or unsubstituted 5 membered heteroalkyl and $R^{17}$ is =O or methyl. In embodiments, $R^6$ is $R^{16}$-substituted 5-8 membered heteroaryl, $R^{16}$ is $R^{17}$-substituted or unsubstituted $C_1$-$C_3$ alkyl and $R^{17}$ is unsubstituted morpholinyl. In embodiments, $R^6$ is $R^{16}$-substituted 5-8 membered heteroaryl and $R^{16}$ is unsubstituted $C_1$-$C_3$ alkyl. In embodiments, $R^6$ is $R^{16}$-substituted triazolyl, tetrazolyl, pyrrolyl, pyrridinyl or oxodiazolyl.

In embodiments, the compound of formula (I) has the formula:

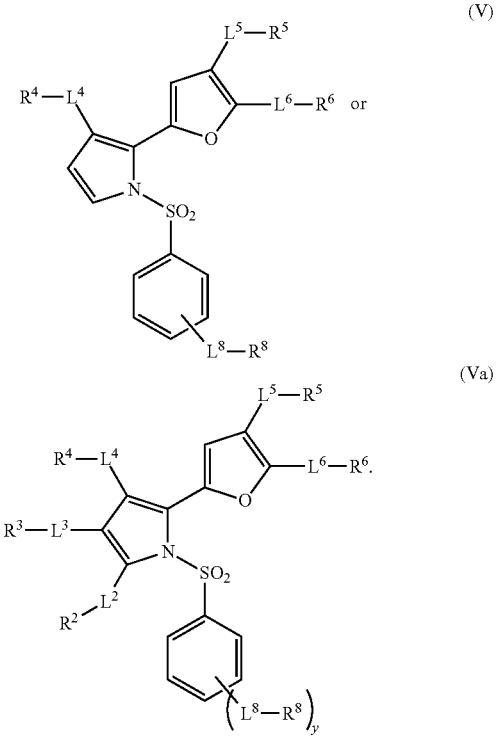

Regarding Formula (V) and (VA), $L^8$ is independently a bond, —C(O)—, —C(O)O—, —OC(O)—, —C(O)NR$^7$—, —NR$^7$C(O)—, —O—, —S(O)$_{n9}$—, —S(O)NR$^7$—, —NR$^7$—, OR$^7$OP(O)—, NR$^7$S(O)$_2$—, —(NR$^7$)NP(O)—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene. The variable n9 is 0, 1 or 2 (e.g, 1 or 2). $R^8$ is independently hydrogen, halogen, —N$_3$, —CF$_3$, —CCl$_3$, —CBr$_3$, —CI$_3$, —CN, —CHO, =O, —OR$^{8A}$, —NR$^{8B}$R$^{8C}$, —COOR$^{8A}$, —CONR$^{8B}$R$^{8C}$, NO$_2$, SR$^{8D}$, —SO$_{n8}$R$^{8B}$, —SO$_{n8}$OR$^{8B}$, —SO$_{n8}$NR$^{8B}$R$^{8C}$, —NHNR$^{8B}$R$^8$, —ONR$^{8B}$R$^8$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{8A}$, $R^{8B}$, $R^{8C}$, and $R^{8D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n8 is 1, 2, 3, 4, or 5. y is 1, 2, 3, 4, or 5.

In embodiments, $R^{1A}$, $R^{2A}$, $R^{3A}$, $R^{4A}$, $R^{5A}$, $R^{6A}$, $R^{1B}$, $R^{2B}$, $R^{3B}$, $R^{4B}$, $R^{5B}$, $R^{6B}$, $R^{1C}$, $R^{2C}$, $R^{3C}$, $R^{4C}$, $R^{5C}$, $R^{6C}$, $R^{1D}$, $R^{2D}$, $R^{3D}$, $R^{4D}$, $R^{5D}$, $R^{6D}$, $R^7$, $R^8$, $R^{8A}$, $R^{8B}$, $R^{8C}$, and $R^{8D}$ are independently hydrogen, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

$R^{23}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

$R^{24}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $L^1$, $L^2$, $L^3$, $L^4$, $L^5$, $L^6$, $L^7$ and $L^8$ are independently a bond, —C(O)—, —C(O)O—, —C(O)NH—, —O—, —S(O)$_n$—, —S(O)NH—, —C(O)NHS(O)$_2$—, —NH—, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

$R^{25}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

$R^{26}$ is independently halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

Further regarding compounds with structure of Formulae (IV), (IVA), (V) or (VA), in embodiments $R^8$ is hydrogen, halogen, or substituted or unsubstituted alkyl.

In another aspect, there is provided a pharmaceutical composition including a compound with structure of any one of Formulae (I), (II), (III), (IV), (IVA), (V) and (VA), or embodiment thereof, and a pharmaceutically acceptable excipient.

In another aspect, there is provided a method of treating cancer in a subject in need thereof. The method includes administering an effective amount of a compound with structure of any one of Formulae (I), (II), (III), (IV), (IVA), (V) and (VA), or embodiment thereof, to the subject. In embodiments, the cancer is leukemia.

In another aspect, there is provided a method of antagonizing Mcl-1. The method includes contacting a Mcl-1 mixture with a compound with structure of any one of Formulae (I), (II), (III), (IV), (IVA), (V) and (VA), or embodiment thereof.

In embodiments, the compound of formula (I) has the formula:

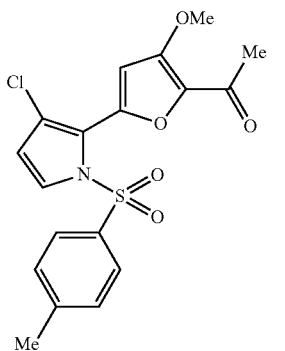
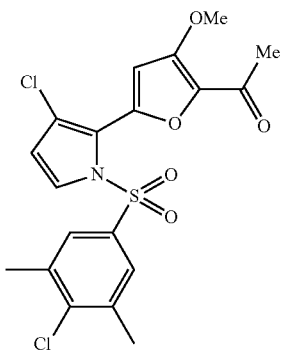
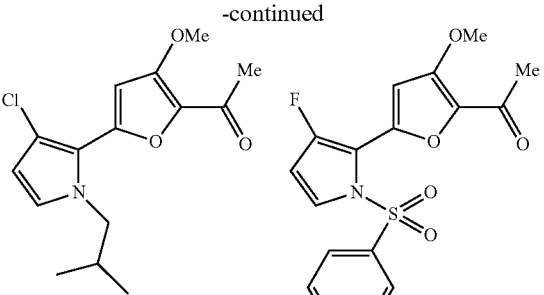
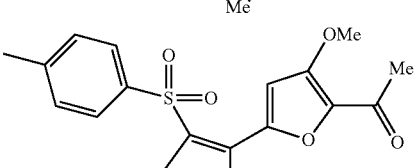
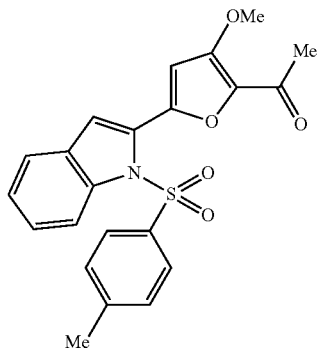
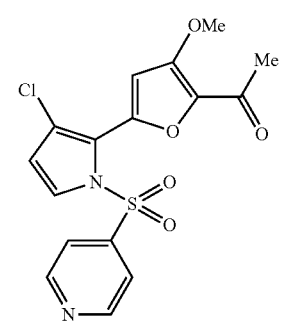
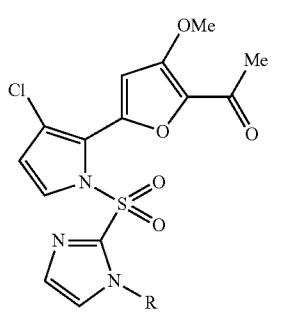
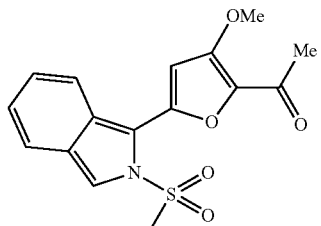
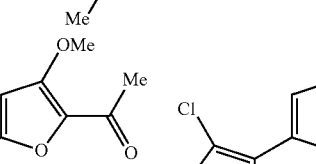
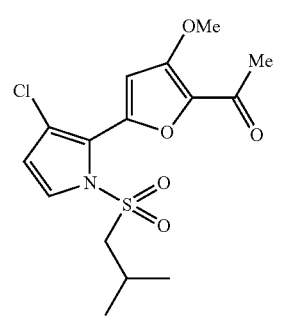
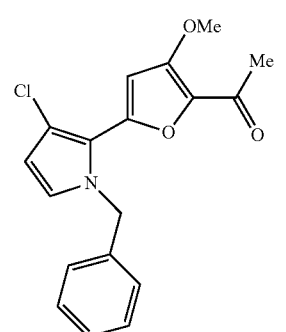
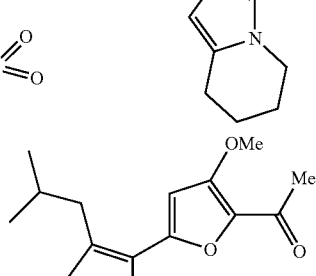

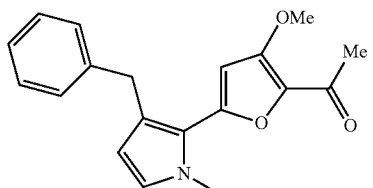
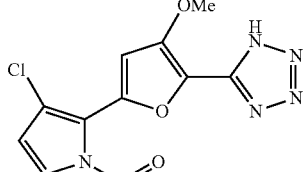
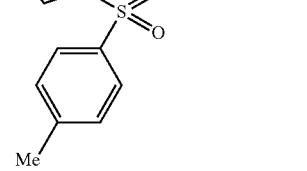
Z, Y, X = N, C, CO
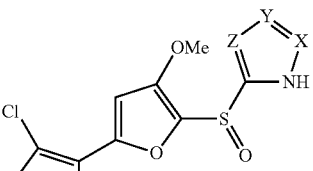
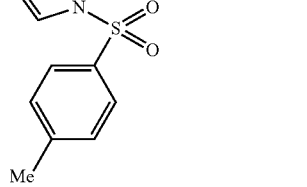
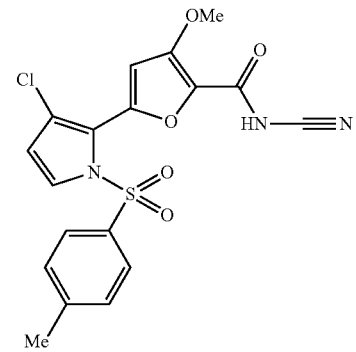
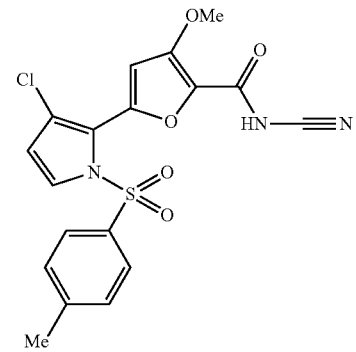
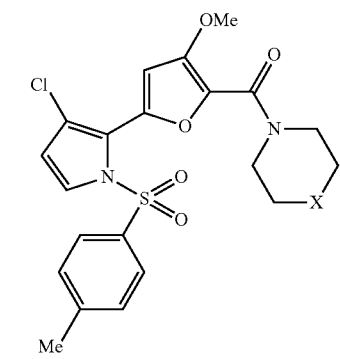
X = S, NR, O
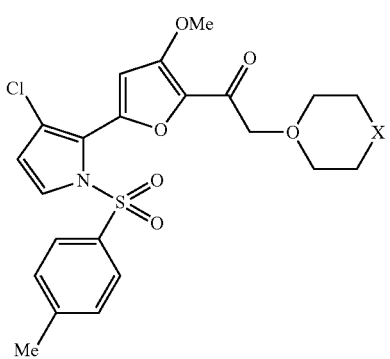
X = NR, S, O

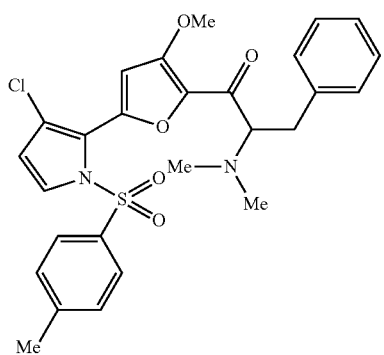
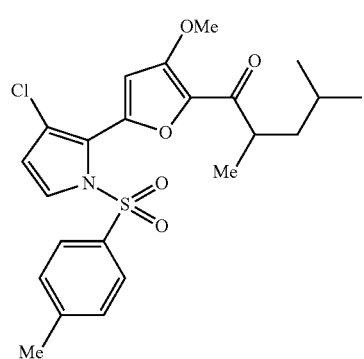
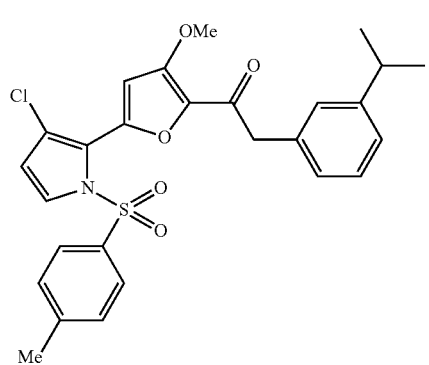
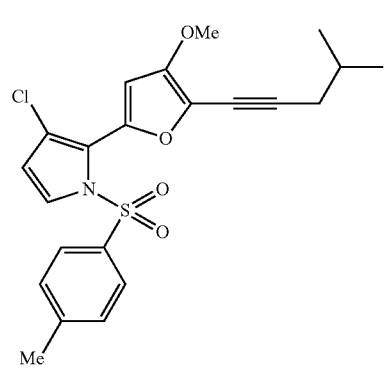
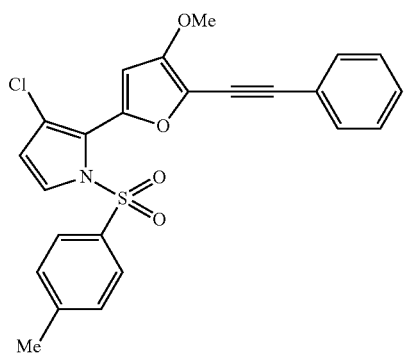
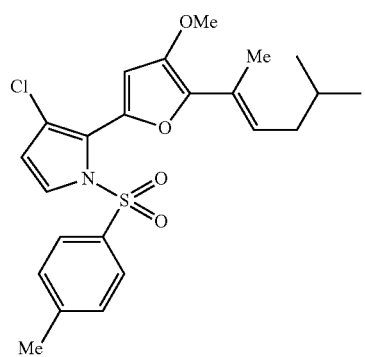
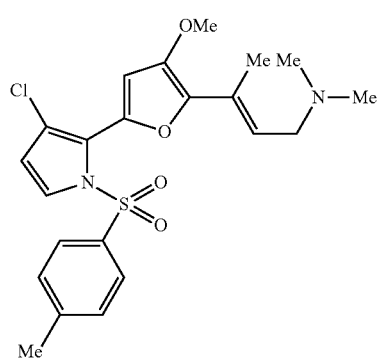
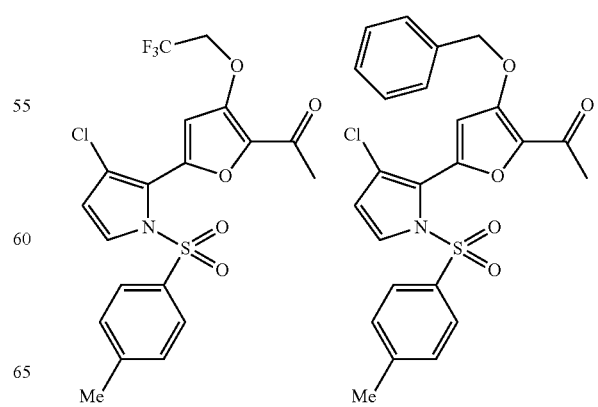

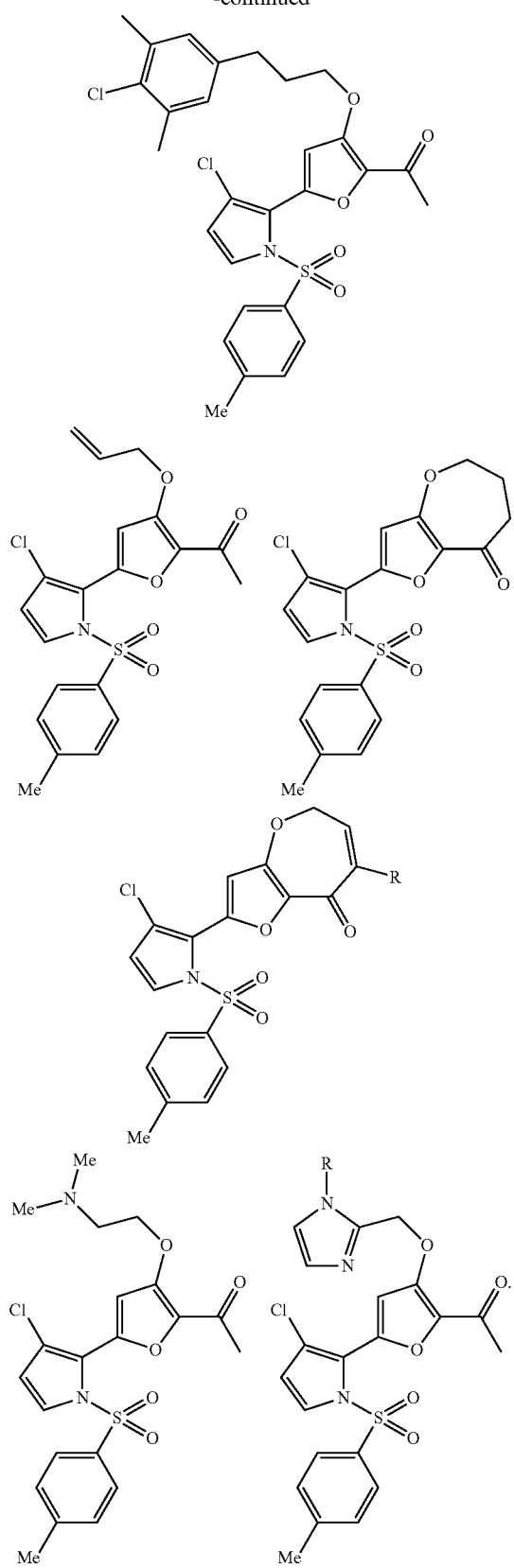
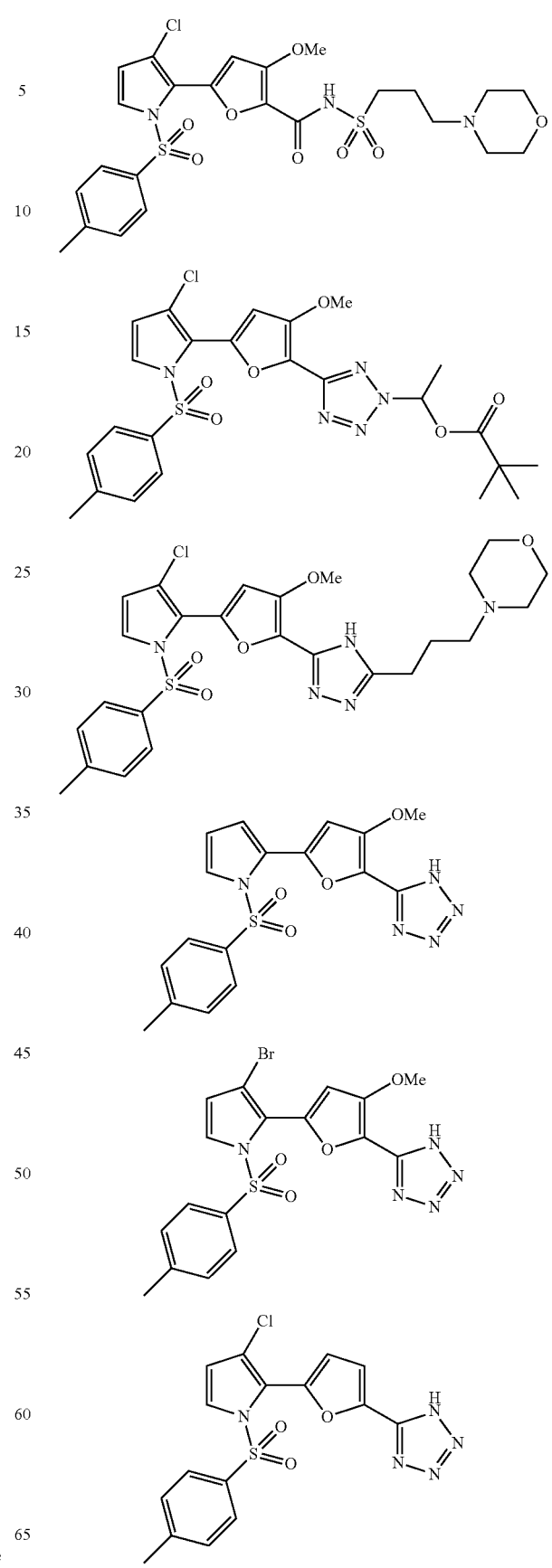
In embodiments, the compound of formula (I) has the formula:

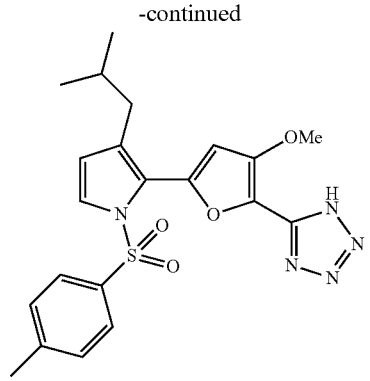
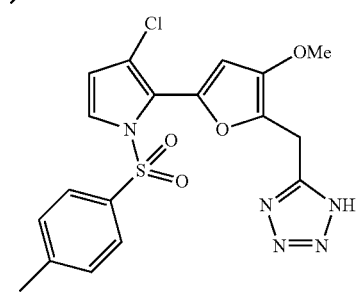
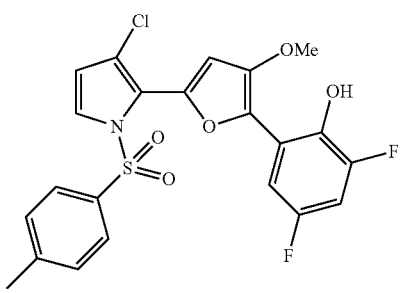
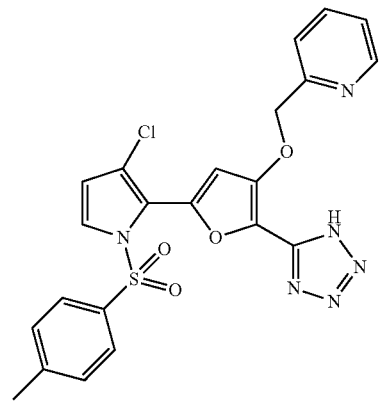
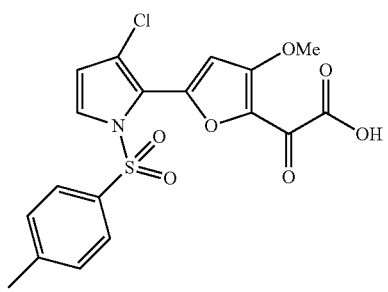
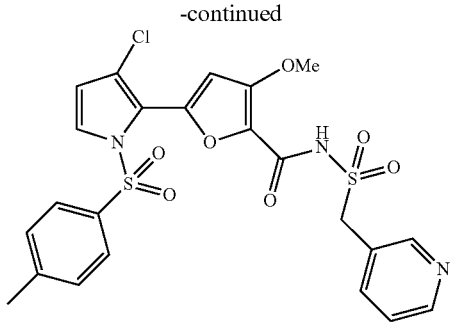
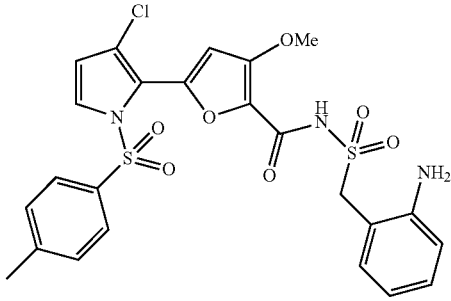
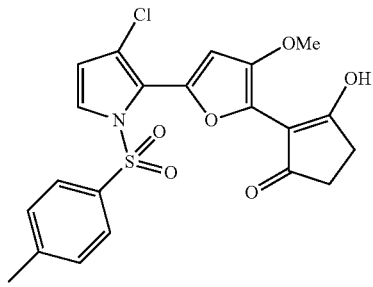
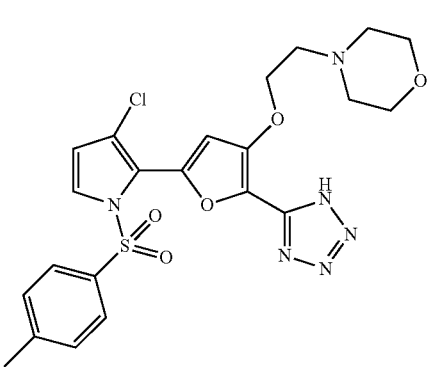
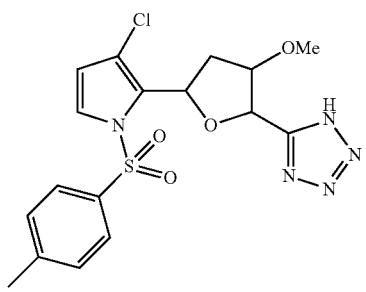

-continued
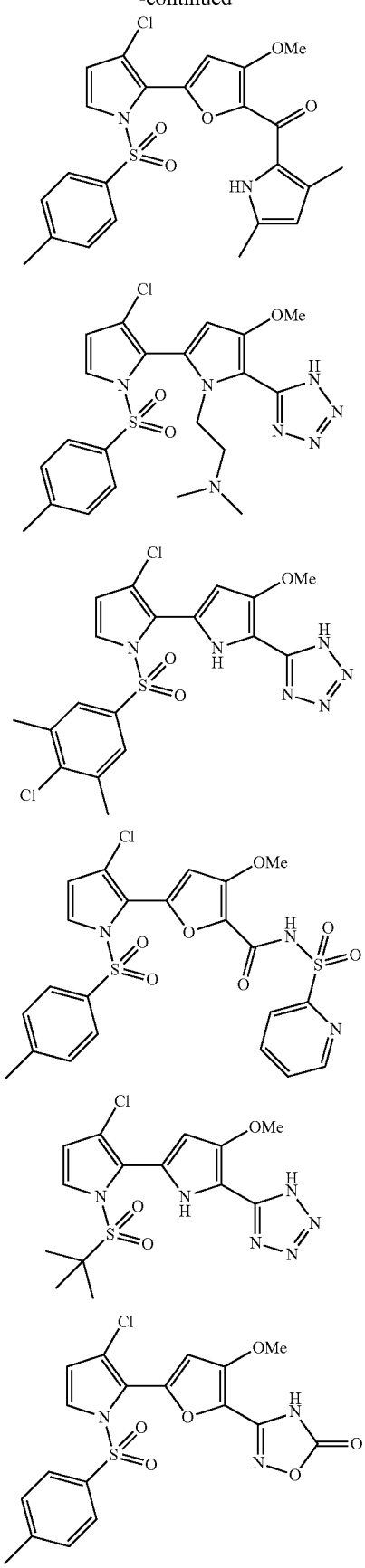
-continued
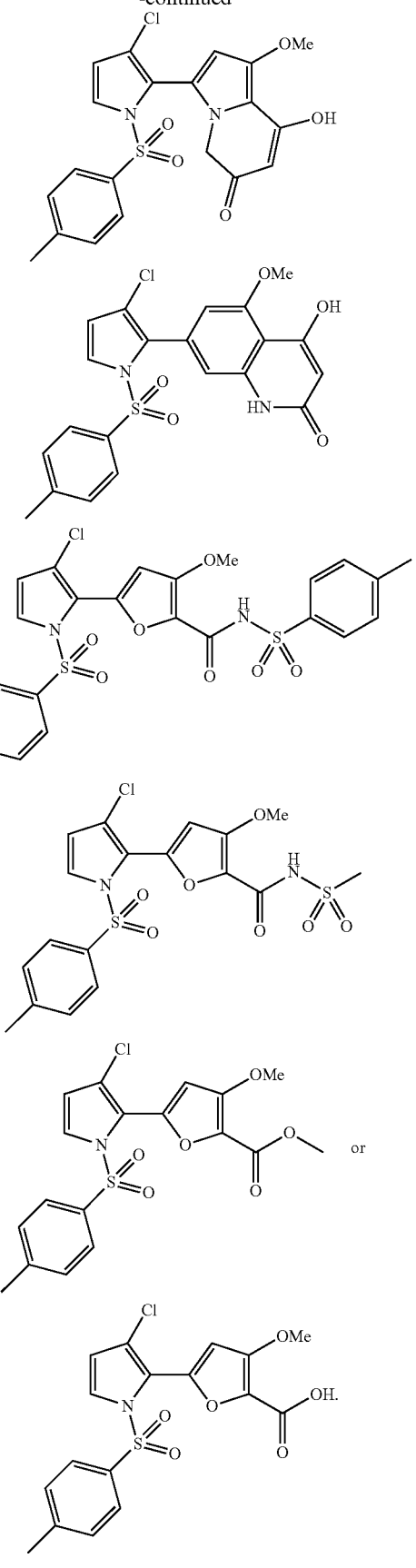
or

Also provided herein is a method of treating cancer in a subject in need thereof by administering an effective amount of a compound as described herein (e.g. formula (I), (II), (III), (IV), (IVA), (V) and (VA), including embodiments thereof, to the subject. The cancer is as described herein, including embodiments thereof listed above. In embodiments, the cancer is leukemia.

Also provided herein are methods of antagonizing Mcl-1, by contacting an Mcl-1 with a compound as described herein (e.g. formula (I), (II), (III), (IV), (IVA), (V) and (VA), including embodiments thereof. In embodiments, the Mcl-1 is within a mixture within a reaction vessel. In other embodiments, the Mcl-1 is with in a cell. In other embodiments, the Mcl-1 is with in a cell extract.

EXAMPLES

Example 1

The vast majority of existing cancer chemotherapeutics ultimately kill tumor cells by triggering the intrinsic pathway of apoptosis.4 At the cellular level, this proteolytic cascade is controlled by the Bcl-2 family of proteins, which are responsible for perturbing the integrity of the mitochondrial membrane in response to cellular stress.5 Bcl-2 proteins are classified as either pro-death or pro-survival, and the balance between these opposing groups regulates intracellular death decisions.6 The pro-survival Bcl-2 members (Bcl-2, Bcl-$X_L$, Bcl-w, Mcl-1, and A1) inhibit the function of multi-domain pro-death Bcl-2 proteins Bak and Bax, which reside on or near the mitochondria. This cytoprotective blockade is regulated through well-characterized protein-protein interactions (PPI's) between four regions of high sequence similarity known Bcl-2 homology (BH1-4) domains.7 In response to cellular stress (e.g. DNA damage), transcription of a second group of pro-death Bcl-2 members is activated. These proteins (Bim, Bad, tBid, Puma, and Noxa) share a helical BH3 peptide that functions as exogenous death ligand. Docking of the BH3 helix to a hydrophobic groove on the surface of pro-survival members neutralizes their cytoprotective action. This releases Bax and Bak, which form pores in the mitochondria and initiate apoptosis by releasing apoptogenic factors (e.g. cytochrome c and SMAC) into the cytosol that trigger downstream caspase activation.

Cancer cells have evolved mechanisms to evade intrinsic apoptosis, allowing these damaged cells to gain additional tumorigenic features. The overexpression of pro-survival Bcl-2 members is a critical factor for disease maintenance in many human cancer types.8 Elevated levels are correlated with resistance to chemotherapeutic agents and an aggressive malignant phenotype.9, 10 These proteins have therefore emerged as highly relevant targets for new cancer therapies; however, effective small-molecule inhibitors have been difficult to develop. The design of pan-Bcl-2 inhibitors is complicated because pro-survival Bcl-2 proteins are divided into two structurally distinct subgroups, one comprising Bcl-2, Bcl-$X_L$, and Bcl-w, and the other comprising Mcl-1 and A1. Full induction of apoptosis requires the neutralization both subgroups. 11 NMR-based structural biology efforts have resulted in the development of the small-molecule Bcl-2/Bcl-$X_L$ inhibitor ABT-737 and its analog ABT-263, which have advanced to human clinical trials. 12,13 While these compounds have in vivo activity in tumors dependent on Bcl-2 and Bcl-$X_L$, the overexpression of Mcl-1 serves as a major resistance mechanism.

Mcl-1 is highly expressed in a variety of tumors and amplification of the Mcl-1 locus is one of the most frequent somatic genetic events in human cancer. 14 As such, the development of small-molecule Mcl-1 inhibitors has emerged as a vibrant area of cancer research. However, there are no reports of selective Mcl-1 inhibitors that have advanced to clinical trials. Agents with tailored specificity for Mcl-1 would provide finely tuned therapies to treat distinct cancer types while potentially avoiding unwanted side effects, especially when used in combination therapy. In addition, such compounds would serve as invaluable research tools to dissect the differential biological functions of pro-survival proteins through cell biology.

Applicants recently initiated a program aimed at exploring the capacity of prodiginine natural products to selectively antagonize the Bcl-2 protein-protein contacts that regulate intrinsic apoptosis. 15 In collaboration with Prof. Gordon Shore at the Morris Goodman Cancer Research Center (McGill University, Canada), Applicants have developed a synthetic small-molecule with the capacity to antagonize the Mcl-1/Bak PPI in a cell-free functional assay. This lead structure, herein referred to JHF3056, is cytotoxic at micromolar concentrations to human myeloid leukemia cells (KMS-11) in which cell survival is dependent on Mcl-1 overexpression. This compelling in vitro data directly translates to anti-tumor activity in vitro. JHF3056 is nontoxic at pharmacologically relevant doses (minimum toxic dose=80 mg/Kg) and sensitizes lymphoma tumor xenografts to doxorubicin in an isogenic mouse model. Taken together, these preliminary data suggest that JHF3056 and related structures are potential Mcl-1 inhibitors with direct and immediate application to human cancer. Specifically, JHF3056 has application as treatment for human breast and non-small cell lung cancer carcinomas, where Bcl-$X_L$ is expressed at low-levels and Mcl-1 overexpression is required for disease maintenance. 16

Despite the challenge of designing a small-molecule that targets the extend protein-protein interfaces involved in antagonism of pro-survival Bcl-2 proteins, efficacious BH3 mimetics can be developed. The prototype small molecule ABT-737 (1) and its orally available analog ABT-263 (2) represent the best extant examples of small-molecules that mimetic the BH3 α-helix (FIG. 1). These compounds, modeled after the BH3 peptide of Bim, were designed using NMR structure-based methods at Abbott and Genentech. ABT-737 inhibits Bcl-2, Bcl-$X_L$, and Bcl-w, at nanomolar concentrations. The X-ray structure of 1 in complex with Bcl-$X_L$ highlights the binding of this mimetic to the hydrophobic groove of Bcl-$X_L$. As a result, 1 induces apoptosis in select cancer types driven by overexpression of these proteins. This seminal work has driven the recent structure-based design of related BH3 mimetics 3 and 4, which also exhibit strong antitumor activity in vivo against cancers where Bcl-2/Bcl-$X_L$ are overexpressed. The preclinical success of 1-4 provides strong proof-of-concept for further development in this area.

One important limitation of mimetics 1-4 is their inability to engage Mcl-1.17 Consequently, 1-4 are not broadly cytotoxic as a single agents and exhibit poor activity in cancer types with high endogenous levels of Mcl-1.18 Although the development of Mcl-1 inhibitors has been of considerable interest, efficacious small molecules have not entered the clinic. Walensky and colleagues have reported that 'stapled' Mcl-1 BH3 peptides are effective Mcl-1 inhibitors in preclinical trials. Several other small-molecules that reportedly inhibit Mcl-1 have been described. Cohen and coworkers have shown that among them only 2, BI-97C1

(5), MIM-1 (6), and TW-37 (7) are able to target Mcl-1 and induce apoptosis via the intrinsic pathway in vitro (FIG. 1). Very recently, Fesik and coworkers have reported that small-molecule 8 has potent affinity for recombinant Mcl-1 in vitro. An X-ray crystal structure of this compound in complex with Mcl-1 is reported, however, no preclinical cellular data is available.

The most successful extant small-molecule antagonist of Mcl-1 in vivo is obatoclax (9). This pan-Bcl-2 inhibitor advanced to human clinical trials and is able to overcome Mcl-1-mediated resistance to apoptosis in cancer cell lines where ABT-737 (1) is ineffective. Unfortunately, this compound also exhibits off mechanism cytotoxicity and has been shown to trigger apoptosis in the cells where the genes for Bax and Bak have been genetically deleted. Thus, obatoclax does not exclusively function as a Mcl-1 antagonist in vivo JHF3056 (10) is a synthetic small-molecule derived from the heterocyclic side-chain of (+)-roseophilin. This bioactive substance directly antagonizes Mcl-1 in a functional assay and exhibits sub-micromolar cytotoxicity to human cancer cells dependent on Mcl-1 overexpression for survival. Moreover, we've evaluated 10 in a leukemia mouse model. Applicants' compound exhibits clear anti-tumor activity in combination with the chemotherapeutic doxorubicin in vivo. Key data and comparison of 10 relative to existing lead Mcl-1 inhibitors 8 and 9 is summarized below.

Figures 2, 2A, 2B:
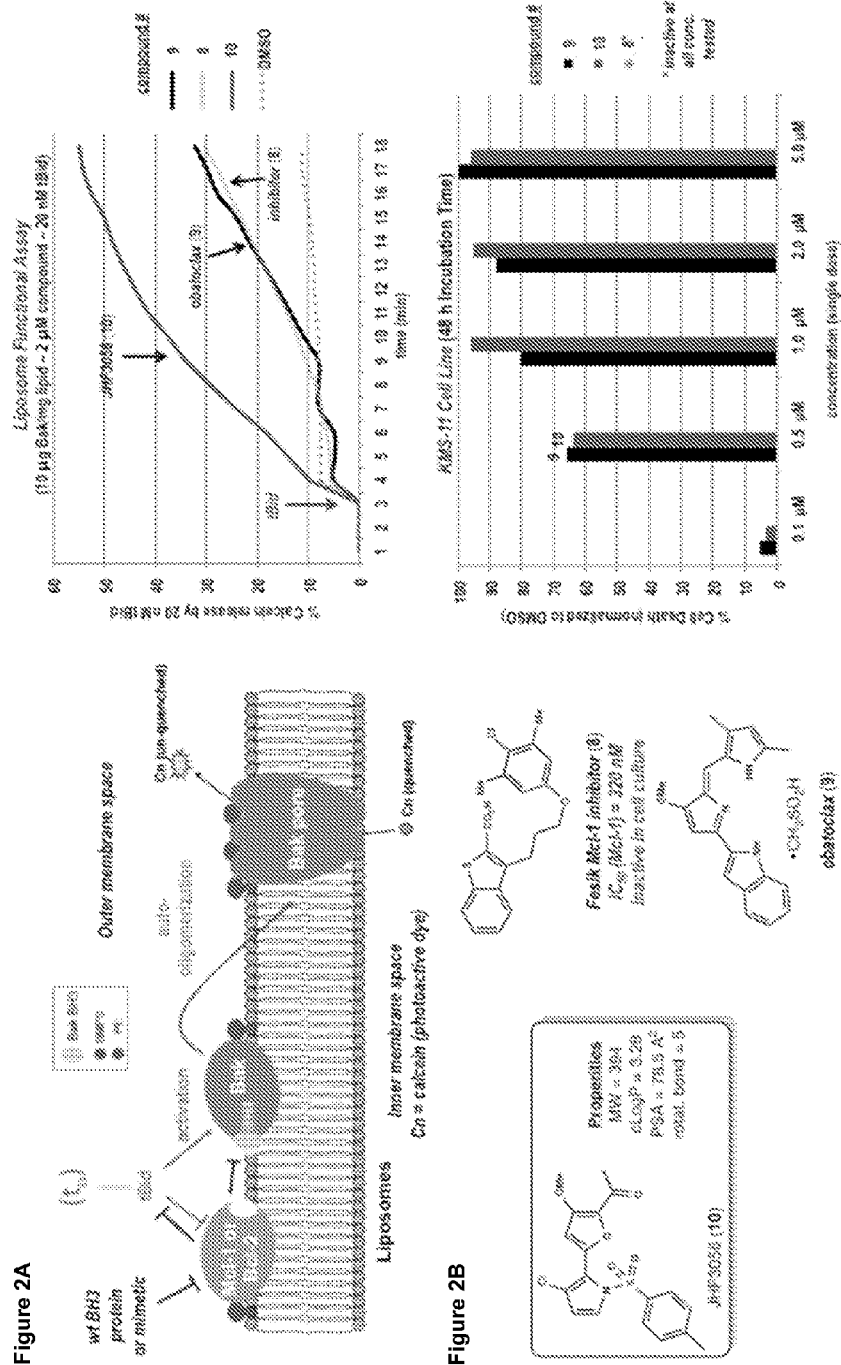
FIGS. 2A-2B. In vitro data for 10 and comparison to reported Mcl-1 inhibitors 8 and 9.

In vitro data. In vitro data for JHF3056 (10) in a liposome assay and in cell culture is summarized in FIG. 2. The Shore lab has developed a functional assay utilizing recombinant proteins anchored in artificial liposomes that enables the evaluation of small-molecules to disrupt the Mcl-1/Bak PPI (FIG. 2A). In this assay, full-length functional single cysteine mutants of Mcl-1 and Bak were anchored into lipids (with PE's) utilizing the engineered cysteine residues as a handle. This allows Applicants to recapitulate Bak-mediated mitochondrial permeabilization and measure the various protein-protein and protein-membrane interactions involved in Mcl-1 regulation of Bak. The release of calcenin (Cn) dye encapsulated in the liposome was used to quantify membrane permeabilization. When the system is untreated, Mcl-1 sequesters Bak by engaging its BH3 domain. Incubation with an active inhibitor neutralizes Mcl-1. This triggers Bak auto-oligomerization resulting in the formation of pores in the lipid membrane and release of Cn. By measuring UV emission from Cn, Applicants can quantify antagonism of Mcl-1 in real time.

Compound 10 exhibits promising activity in this functional assay. To gauge its performance, Applicants compared results using 10 to Fesik's compound 8 and obatoclax (9). The superior performance of JHF3056 (10) relative to 8 and 9, two of the most promising Mcl-1 inhibitors reported to date, is apparent. Based on these results, Applicants evaluated the cytotoxicity of 10 in cell culture against human KMS-11 myeloid leukemia cells, which require overexpression of Mcl-1 for survival. Compound 10 exhibits sub-micromolar single dose cytotoxicity against this cell line. Moreover, 10 shows enhanced activity relative to obatoclax (9) at 1.0 μM concentration. Reported Mcl-1 inhibitor 8 was inactive at all concentrations tested. This finding is significant because obatoclax has advanced to phase 2 human clinical trials as combination therapy for human leukemia. Importantly, JHF3056 (10) is a stable solid with promising drug-like properties and lacks the structural liabilities that contribute to off-mechanism cytotoxicity with 9.

Figure 3:
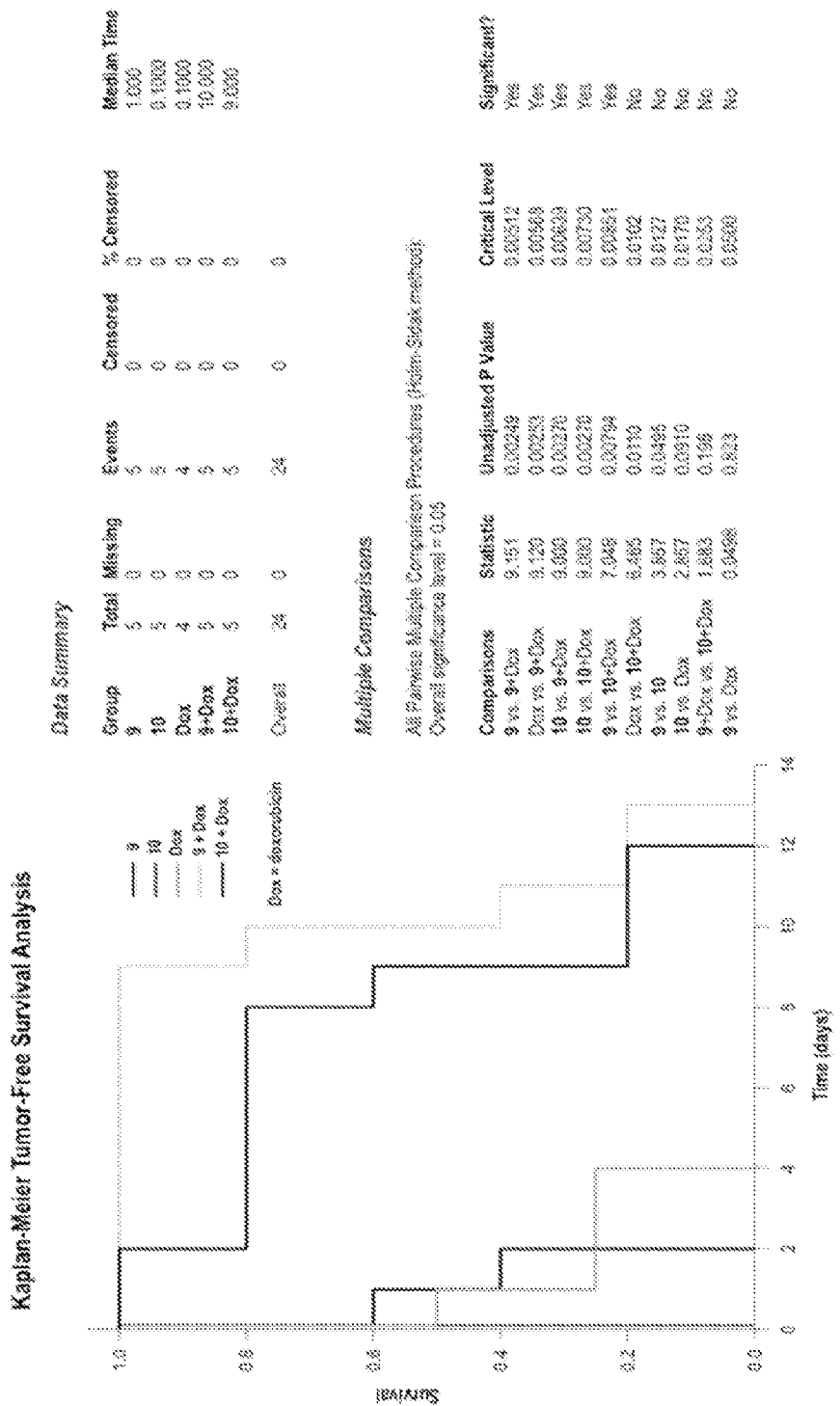
FIG. 3. Comparison of invention 10 (JHF3056) and reported pan-Bcl-2 inhibitor 9 (obatoclax) with and without doxorubicin in mouse lymphoma model.
Figure 4:
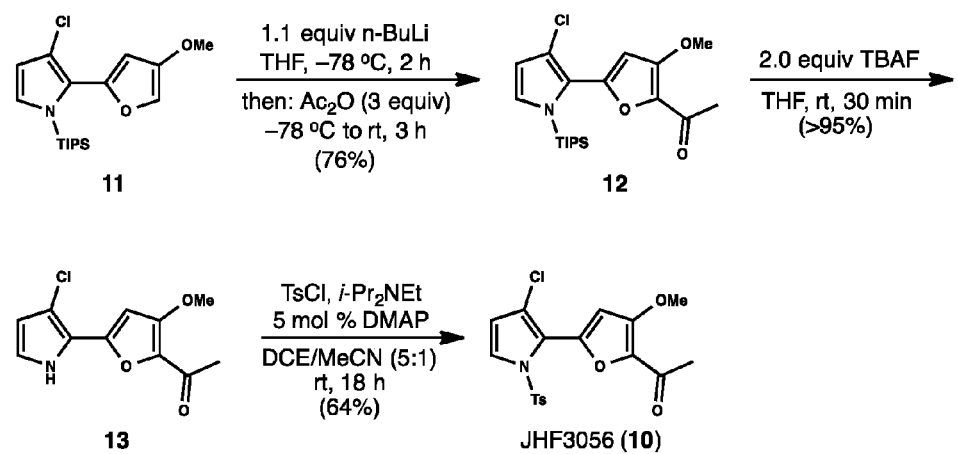
FIG. 4. Synthesis of JHF3056 (10) from known compound 11.
Figure 5:
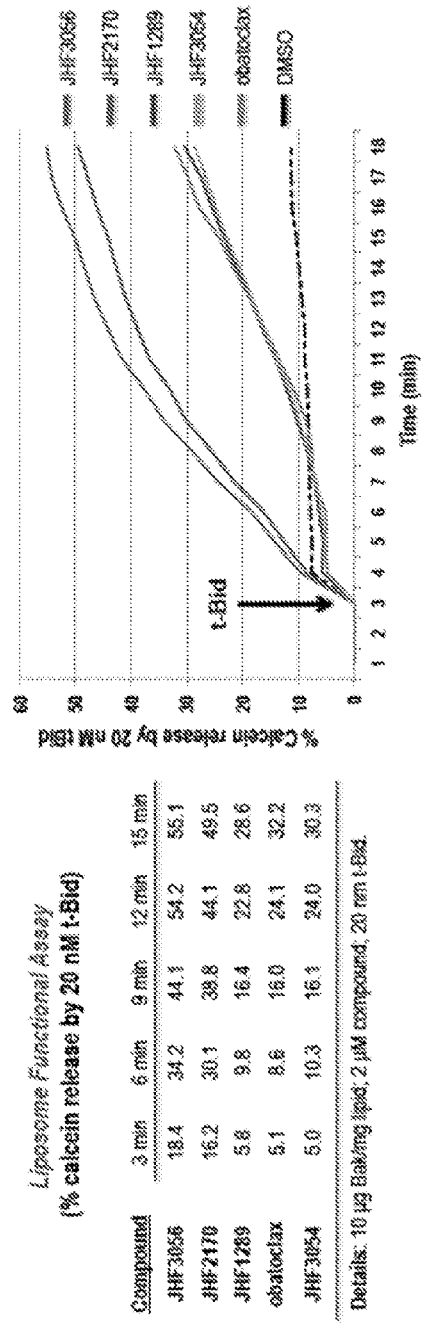
FIGS. 5A-5B. Data for active substances tested to date and comparison to obatoclax (9).
Figure 5:
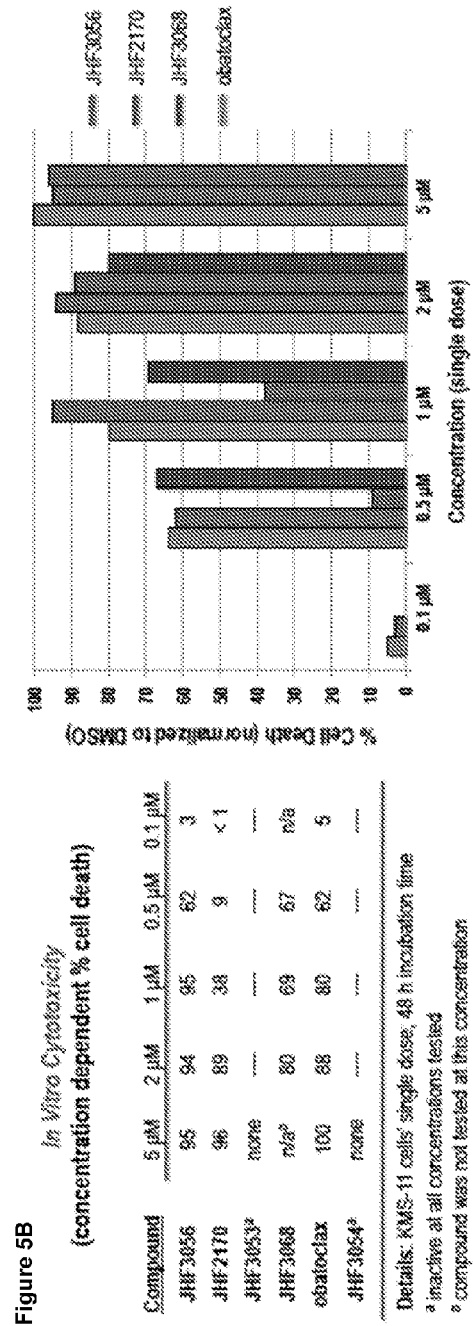

In vivo data. C57BL/6 mice were tail-vein injected with Eμ-myc (myr) Akt lymphoma cells and palpable tumors (multiple sites per animal) allowed to develop. Animals were randomized for tumor burden and treated by intraperitoneal (IP) injection with vehicle, or vehicle containing obatoclax (10 mg/kg) or JHF3056 (40 mg/kg) daily×5. In addition, animals received a single injection of doxorubicin (IP, 10 mg/kg) on day 2 of the injection regimen, either alone or in combination with the obatoclax (9) or JHF3056 (10) regimen. Animals were allowed to become tumor-free (no observable palpable tumors) and then tumor-free survival was measured (time to re-appearance of tumors). Data for these experiments are summarized in FIG. 3.

Mcl-1 inhibitor JHF3056 (10) is prepared in three steps from known pyrrolylfuran 11 as summarized in Scheme 1.19 Applicants' group has recently published a convenient, five-step synthesis of 11, which allows this heterocycle to be accessed on gram-scale (Frederich, J. H.; Matsui, J. K.; Chang, R. O.; Harran, P. G. *Tetrahedon Lett.* 2013, 2645). To prepare 10, methoxy furan 11 is deprotonated at −78° C. using n-BuLi, treated with acetic anhydride, and warmed to room temperature. This sequence affords ketone 12 in 76% yield. The terminal heterocycle is then deprotected by exposing 12 to anhydrous TBAF to furnish pyrrole 13 in excellent yield. Reacting this material with tosyl chloride, Hunig's base, and catalytic DMAP generates JHF3056 (10) in 64% yield. This route has been utilized to prepare 10 in gram quantities and is sufficiently flexible to incorporate substituents at multiple points around the periphery of this heterocyclic pharmacophore.

1-(5-(3-chloro-1-(triisopropylsilyl)-1H-pyrrol-2-yl)-3-methoxyfuran-2-yl)ethan-1-one (12)

A solution of 11 (2.25 g, 6.36 mmol) in THF (30 mL) was cooled to −78° C. and treated with a 1.6 M solution of n-BuLi in THF (4.4 mL, 7.0 mmol). After 30 min at −78° C., the reaction mixture was treated with freshly distilled $Ac_2O$ (1.8 mL, 19.1 mmol). The resultant green solution was maintained at −78° C. for 1 h then warmed to rt and maintained for 3 h. The reaction was quenched with 5 mL of saturated aq. $NaHCO_3$ and diluted with $H_2O$ (50 mL). The organic layer was separated and the aqueous wash was extracted with EtOAc (3×25 mL). The combined organic extracts were dried over $MgSO_4$ and concentrated. Purification by flash chromatography ($SiO_2$, 20:1 hexanes/EtOAc) afforded 12 (1.91 g, 4.83 mmol, 76%) as a yellow solid: 1H NMR (400 MHz, $CDCl_3$) &: 6.95 (d, J=3.0, 1H), 6.64 (s, 1H), 6.33 (d, J=3.0, 1H), 4.00 (s, 3H), 2.41 (s, 3H), 1.58 (sep, J=7.5, 3H), 1.10 (d, J=7.5, 18H).

1-(5-(3-chloro-1H-pyrrol-2-yl)-3-methoxyfuran-2-yl)ethan-1-one (13)

A solution of 12 (1.66 g, 4.19 mmol) in THF (20 mL) was treated with a 1.0 M solution of anhydrous TBAF in THF (8.4 mL, 8.4 mmol) at room temperature. After 30 min, the reaction was quenched with saturated aq. $NaHCO_3$ (25 mL). The organic material was separated and the aqueous layer was washed with EtOAc (3×25 mL). The combined organic extracts were dried over $MgSO_4$ and concentrated. Purification by flash chromatography ($SiO_2$, 1:1 hexanes/EtOAc) afforded 13 (964 mg, 4.02 mmol, 96%) as a colorless solid: $^1H$ NMR (400 MHz, $CDCl_3$) &: 9.63 (br s, 1H), 6.83 (dd, J=3.4, 2.9, 1H), 6.72 (s, 1H), 6.25 (dd, 3.4, 2.9, 1H), 4.00 (s, 3H), 2.43 (s, 3H).

1-(5-(3-chloro-1-tosyl-1H-pyrrol-2-yl)-3-methoxy-furan-2-yl)ethan-1-one (10)

A solution of 13 (871 mg, 3.63 mmol) and i-$Pr_2NEt$ (0.82 mL, 4.00 mmol) in DCE/MeCN (5:1, 40 mL) was treated with TsCl (761 mg, 4.72 mmol) in a single portion. The reaction was stirred at rt for 5 min, then treated with DMAP (50 mg, 0.40 mmol) in a single portion. The resulting dark solution was maintained at room temperature. After 18 h, the mixture was treated with saturated aq. NaHCO$_3$ (100 mL) and rapidly stirred for 30 min. The organic material was partitioned by adding H$_2$O (50 mL) and separated. The aqueous layer was extracted with EtOAc (3×100 mL). The combined organic extracts were dried over MgSO$_4$ and concentrated. Purification by flash chromatography (SiO$_2$, 3:1 hexanes/EtOAc) afforded 10 (912 mg, 2.32 mmol, 64%) as a pale yellow solid: $^1$H NMR (400 MHz, CDCl$_3$) δ: 7.38 (d, J=8.2, 2H), 7.43 (d, J=3.5, 1H), 7.37 (d, J=8.2, 2H), 6.62 (s, 1H), 6.33 (d, J=3.5, 1H), 3.99 (s, 3H), 2.43 (s, 3H), 2.42 (s, 3H).

References (Example 1)

ABT-733 (1): (a) Oltersdorf, T.; Elmore, S. W.; Shoemaker, A. R.; Armstrong, R. C. et al. An inhibitor of Bcl-2 family proteins induces regression of solid tumors. *Nature*, 2005, 435, 677-681. (b) Lee, E. F.; Czabotar, P. E.; Smith, B. J.; Deshayes, K.; Zobel, K.; Colman, P. M.; Fairlie, W. D. Crystal structure of ABT-737 complexed with Bcl-X$_L$: implications for selectivity of antagonists for the Bcl-2 family. *Cell Death Differ.* 2007, 14, 1711-1713.

ABT-263 (2): Shi, J.; Zhou, Y.; Huang, H.-C. Navitoclax (ABT-263) accelerates apoptosis during drug-induced mitotic arrest by antagonizing Bcl-xL *Cancer Res.* 2011, 71, 4518-4526.

Compound 3: Brady, R. M.; Hatzis, E.; Connor, T.; Street, I. P.; Baell, J. B.; Lessene, G. Synthesis of conformationally constrained benzoylureas as BH3-mimetics. *Org. Biomol. Chem.* 2012, 10, 5230-5237.

Compound 4: Zhou, H.; Aguilar, A.; Chen, J.; Bai, L.; Liu, L.; Meagher, J. L.; Yang, C.; McEachern, D.; Cog, X.; Stuckey J. A.; Wang, S. Structure-based design of potent Bcl-2/Bcl-xL inhibitors with strong in vivo antitumor activity. *J. Med. Chem.* 2012, 55, 6149-6161.

Stapled Mcl-1 BH3 peptides: Stewart, M. L.; Fire, E.; Keating, A. E.; Walenski, L. D. The Mcl-1 BH3 helix is an exclusive Mcl-1 inhibitor and apoptosis sensitizer. *Nat. Chem. Biol.* 2010, 6, 595-601.

Evaluation of reported Mcl-1 inhibitors: Varadarajan, S.; Volger, M.; Butterworth, M.; Dinsdale, D.; Walensky, L. D.; Cohen, G. M. Evaluation and critical assessment of putative Mcl-1 inhibitors. *Cell Death and Differ.* 2013, 20, 1475-1484.

BI-97C1 (5): Wei, J.; Stebbins, J. L. et al. BI-97C1, an optically pure apogossypol derivative as a pan-active inhibitor of Bcl-2 family proteins. *J. Med. Chem.* 2010, 53, 4166-4167.

MIM-1 (6): Cohen, N. A.; Stewart, M. L. et al. A competitive stapled peptide screen identifies a selective small molecule that overcomes Mcl-1 dependent leukemia cell survival. *Chem. Biol.* 2012, 19, 1175-1186.

TW-37 (7): Wang, Z.; Song, W. et al. TW-37, a small-molecule inhibitor of Bcl-2, inhibits cell growth and invasion in pancreatic cancer. *Int. J. Cancer* 2008, 123, 958-966.

Fesik's inhibitor (8): Firberg, A. et al. Discovery of potent Mcl-1 inhibitors using fragment-based methods and structure-based design. *J. Med. Chem.* 2013, 56, 15-30.

Obatoclax (9): (a) Nguyen, M. et al. Small-molecule obatoclax (GX15-070) antagonizes Mcl-1 and overcomes Mcl-1-mediated resistance to apoptosis. *PNAS* 2007, 104, 19512-19517. (b) Obatoclax, Fludarabine, and Rituximab in treating patients with previously treated chronic lymphocytic leukemia ClinicalTrials.gov Identifier: NCT00612612A. (c) Phase I/II of GX15-070MS in untreated CLL ClinicalTrials.gov Identifier: NCT00600964. (d) Murthy, M. S.; Steenaart, N. A. E.; Johnson, R. A.; Shore, G. C. PCT Int. Appl. WO 2001055131, 2001, 267 pp.

Off-mechanism activity of 9: Vogler, M.; Weber, K.; Dinsdale, D.; Schmitz, I.; Schulze-Osthoff, K.; Dyer, M. J. S.; Cohen, G. M. Different forms of cell death induced by putative Bcl-2 inhibitors. *Cell Death Differ.* 2009, 16, 1030-1039.

1 Adams, J. M.; Corey, S. The Bcl-2 apoptotic switch in cancer development and therapy. *Oncogene* 2007, 26, 1324-1337.

2 Danial, N. N.; Korsmeyer, S. J. Cell death: critical control points. *Cell* 2004, 116, 205-219.

3 Hanahan, D.; Weinberg, R. A. Hallmarks of cancer: the next generation. *Cell* 2011, 114, 646-674.

4 Cotter, T. G. Apoptosis and cancer: the genesis of a research field. *Nat. Rev. Cancer* 2009, 9, 501-507.

5 Lessene, G.; Czabotar, P. E.; Coman, P. M. Bcl-2 family antagonists for cancer therapy. *Nat. Rev. Drug Disc.* 2008, 7, 989-1000.

6 Shore, G. C.; Nguyen, M. Bcl-2 proteins and apoptosis: choose your partner. *Cell* 2008, 135, 1004-1006.

7 Petros, A. M.; Olejiniczak, E. T.; Fesik, S. W. Structural biology of the Bcl-2 family of proteins. *Biochim. Biophys. Acta.* 2004, 1644, 83-94.

8 Richardson, A.; Kaye, S. B. Inhibition of the Bcl-2 family of apoptosis regulators as cancer therapy *Curr. Mol. Pharm.* 2008 1, 244-254.

9 Konopleva, M.; Zhao, S.; Hu, W. The anti-apoptotic genes Bcl-X$_L$ and Bcl-2 are overexpressed and contribute to chemoresistance of non-proliferating leukemic CD34$^+$ cells. *Br. J. Haemato.* 2002, 118, 521-534.

10 Poeta, G.; Venditti, A.; Del Principe, M. I. Amount of spontaneous apoptosis detected by Bax/Bcl-2 ratio predicts outcome in acute myeloid leukemia (AML). *Blood* 2003, 101, 2125-2131.

11 Willis, S. N.; Chem, L.; Dewson, G.; Wei, A.; Naik, E.; Fletcher, J. I. Proapoptotic Bak is sequestered by Mcl-1 and Bcl-X$_L$, but not Bcl-2, until displaced by BH3-only proteins. *Genes Dev.* 2005, 19, 1294-1305.

12 Kuroda, J.; Puthalakath, H.; Cragg, M. S.; Kelly, P. N.; Bouillet, P.; Huang, D. C. S.; Kimura, S.; Ottmann, O. G.; Druker, B. J.; Villunger, A.; Roberts, A. W.; Strasser, A. Bim and Bad mediated imatinib-induced killing of Bcr/Abl$^+$ leukemic cells, and resistance due to their loss is overcome by a BH3 mimetic *Proc. Natl. Acad. Sci.* 2006, 103, 14907-14912.

13 Shi, J.; Zhou, Y.; Huang, H.-C. Navitoclax (ABT-263) accelerates apoptosis during drug-induced mitotic arrest by antagonizing Bcl-xL *Cancer Res.* 2011, 71, 4518-4526.

14 Beroukhim, R. et al. The landscape of somatic copy-number alteration across human cancers. *Nature* 2010, 463, 899-905.

15 Frederich, J. H.; Harran, P. G. Modular access to complex prodiginines: total synthesis of (+)-roseophilin via its 2-azafulvene prototropisomer. *J. Am. Chem. Soc.* 2013, 135, 3788-3791.

16 Wei, G. et al. Chemical genomics identifies small-molecule Mcl-1 repressors and Bcl-X$_L$ as a predictor of Mcl-1 dependency. *Cancer Cell* 2012, 21, 547-562.

17 Konopleva, M.; Contractor, R.; Taso, T. et al. Mechanisms of apoptosis sensitivity and resistance to the BH3 mimetic ABT-737 in acute myeloid leukemia. *Cancer Cell* 2006, 10, 375-388.

18 Delft, M. F.; Wei, A. H.; Mason, K. D. et al. The BH3 mimetic ABT-737 targets selective Bcl-2 proteins and efficiently induces apoptosis via Bak/Bax if Mcl-1 is neutralized. *Cancer Cell* 2006, 10, 389-399.

19 Fürstner, A.; Weintritt, H. Total synthesis of roseophilin. *J. Am. Chem. Soc.* 1998, 120, 2817-2825.

Example 2. Tailored Fragments of Roseophilin Selectively Antagonize Mcl-1 In Vitro Compound numbering and references for Example 2 are local to Example 2, to the extent that any compound numbering or references differ from those provided elsewhere herein.

Applicants have discovered a fragment of the natural product roseophilin, a member of the prodiginine family, that antagonizes Mcl-1 functions in a liposome-based assay for mitochondrial membrane permeabilization. By tailoring this substance such that it can participate in salt bridging with the protein surface, Applicants have prepared the first prodiginine inspired structure that shows direct, saturable binding to a recombinant Bcl-2 family member in vitro.

Applicants' laboratory is interested in small molecule mimics of regulatory proteins. Compounds that can restore apoptotic signaling in cancer cells are a particular focus. Applicants described the first Smac mimetics in 2004.[1] Those molecules subsequently helped identify compounds that activate the TRAIL receptor.[2] The TRAIL/Smac mimetic combination selectively stimulates apoptosis by de-repressing caspase activities.[3] Attention has recently shifted to a second mechanism that results in apoptosis being suppressed in cancer; namely, the failed release of pro-apoptotic factors (including Smac) from the outer membrane space of mitochondria as gated by Bcl-2 proteins. Pro-survival Bcl-2 proteins prevent pore formations in the mitochondrial membrane needed to propagate apoptosis. Bcl-2 activities are countered by interactions with 'BH3-only' regulatory proteins—which involve key α-helix/domain interactions. These contacts have been studied intensely for two decades.[4] Early screens by one of Applicants (GCS) identified the bacterial pigment streptorubin B (1, FIG. 6) as an inhibitor of the Bcl-2/Bax interaction.[5] This discovery led to the development of obatoclax (2), a simplified indolic variant of 1 that entered human clinical trials as a pan Bcl-2 antagonist.[6] In functional settings, obatoclax promotes apoptosis by countering activities of anti-apoptotic Bcl-2 family members, including myeloid cell leukemia protein 1 (Mcl-1). Mcl-1 based resistance has limited other Bcl-2 inhibitor programs.[7]

Obatoclax is a valuable structure, but it does have liabilities. Its pyrrolylpyrromethene core can generate reactive oxygen species when bound by copper[8] and, in protonated form, it can function as a chloride ion symporter.[9] In an attempt to identify variants of 2 lacking these activities, Applicants looked to Applicants' recent synthesis of roseophilin (3)[10] for candidates. The heterocyclic domain of 3 harbors a furan in place of the central pyrrole present in 1 and 2. Applicants anticipated the coordination chemistries of roseophilin-type substances would differ markedly from obatoclax.

Figure 6:
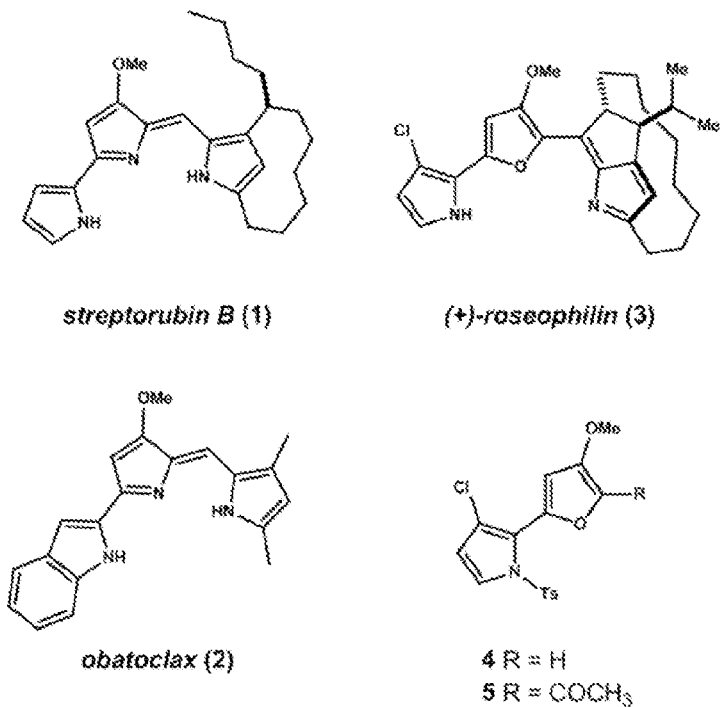
FIG. 6. Obatoclax (2) and roseophilin segment 5, in contrast to roseophilin (3), counter Mcl-1 activity and promote Bak-mediated permeabilization of liposomal membranes. Data normalized to DMSO control.
Figure 6:
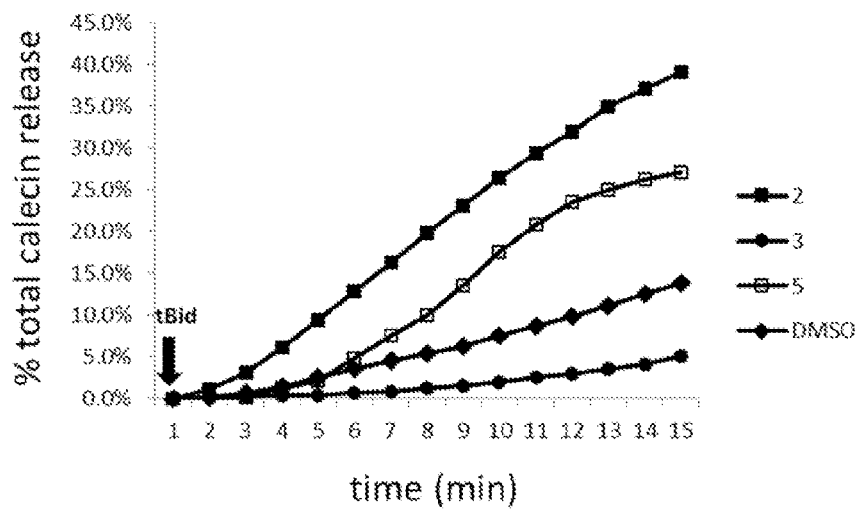

Synthetic 3, along with numerous intermediates and their derivatives were assayed in a model system for mitochondrial outer membrane permeabilization (MOMP). This liposome based experiment recapitulates a signaling axis involving pro-apoptotic Bak, anti-apoptotic Mcl-1, and an active, truncated 15 kDa subunit of the pro-death protein Bid (tBid).[11] Bak and Mcl-1 are transmembrane proteins constitutively anchored in the mitochondrial outer membrane. tBid translocates to mitochondria upon cleavage of Bid by caspase-8 and stimulates MOMP by directly activating free Bak and by disengaging any activated Bak from Mcl-1. Applicants' assay mimics these events using recombinant, lipidated Mcl-1 and Bak that are constitutively bound to unilamellar liposomes encapsulating calcein dye. tBid addition initiates Bak homo oligomerization and pore formations, which in turn results in calcein release and a fluorescence signal. Mcl-1 counters this tBid dependent activation of Bak, which is overcome by small molecule Mcl-1 antagonists (FIG. 6).

The majority of compounds Applicants screened in this assay behaved like roseophilin itself. Namely, they showed little activity. However, an N-tosylated derivative of the pyrrolylfuran segment of the natural product did function in this format. At 2 μM concentrations (vs. 0.4 μM Mcl-1 in liposomes), compound 4 caused calcein release at a rate approaching that of obatoclax (data not shown). Additional experiments with 4 were complicated by its limited stability. However, acetylated variant 5 was a bench stable solid (m.p.=162-165° C.) that was near equipotent to 4 in the liposome assay (FIG. 6).[13]

Figure 7:
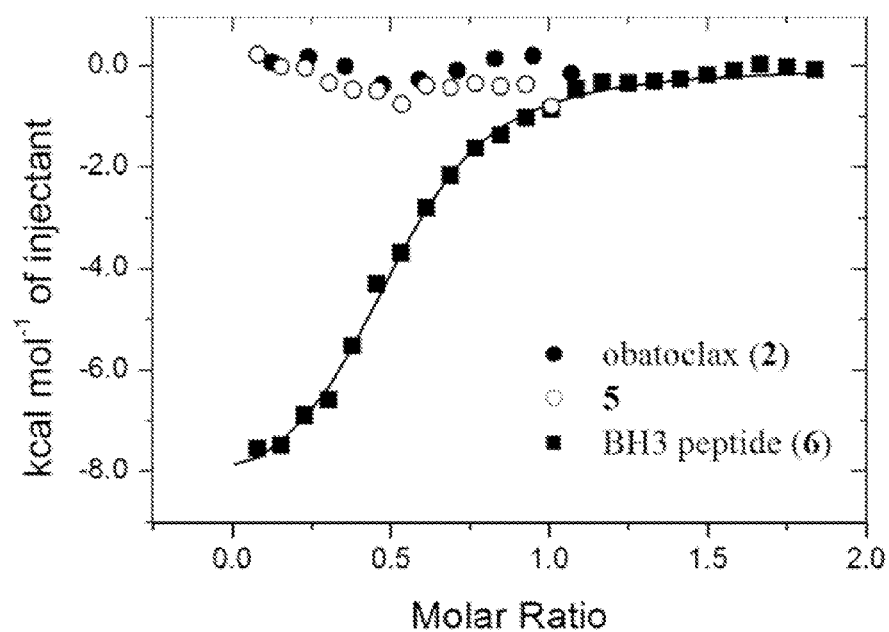
FIG. 7. A peptide corresponding to the Mcl-1 BH3 domain (6, Ac-KALETLRRVGDGVQRNHETAF-$CONH_2$) (SEQ ID NO:1) binds Mcl-1 in vitro ($K_D$=1.1±0.06 μM). See reference 12 of Example 2. Neither compound 5 nor obatoclax (2) exhibit similar behavior. Titration microcalorimetry data shown are averaged values from triplicate analyses.

An intriguing characteristic of obatoclax was that it blocked functions of Mcl-1 and other anti-apoptotic Bcl-2 proteins in membrane environments, yet showed limited/variable affinity for those proteins in isolation.[14] Applicants asked whether this was also true of 5. Recombinant Mcl-1 was expressed and purified from *E. coli*. Applicants synthesized a 21-residue helical peptide from the BH3 domain of Mcl-1 and used that oligomer as a positive control for isothermal titration microcalorimetry (ITC) experiments.[12] Neither 2 nor 5 demonstrated measurable affinity for Mcl-1 by ITC (FIG. 7). Compound 5 did not induce release of calcein from liposomes lacking Mcl-1, suggesting its effects were not derived from interactions with Bak. Likewise, the compound showed no binding to truncated Bid (data not shown)—prepared by cleaving the full-length protein with TEV protease.[15] Like obatoclax, the functional attributes of 5 were not easily traceable to a binding event with isolated protein.

Figure 8A:
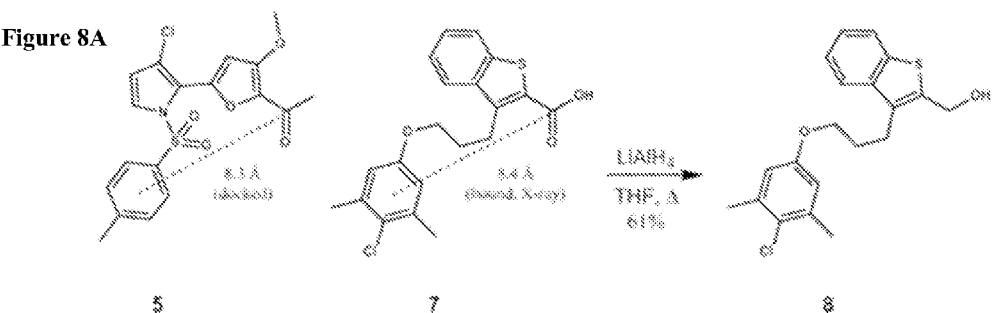
FIGS. 8A-8D.
Figure 8B:
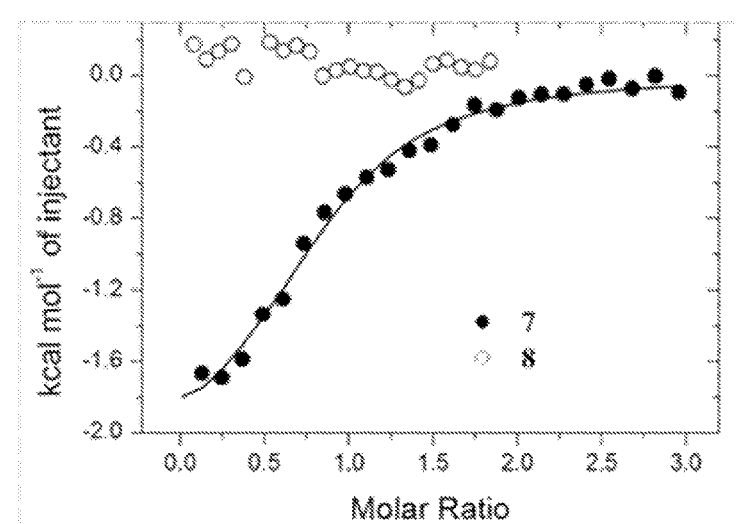
Figure 8C:
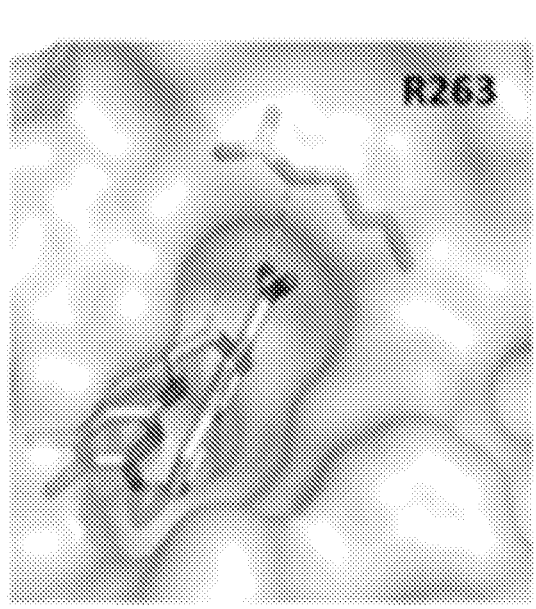

In 2013 Fesik reported a small molecule having quantifiable affinity for purified Mcl-1.[16] Benzothiophene carboxylate 7 (FIG. 8A) was identified using Fesik's seminal fragment-based discovery methods.[17] X-ray co-crystallography showed the compound inserted into a binding pocket beneath the groove used by BH3 helical peptides to bind at the Mcl-1 surface (FIG. 8C). Its carboxylic acid lay at the mouth of this pocket and formed a salt-bridge with R263—an interaction normally made from the opposite direction by a conserved aspartic acid residue in BH3 peptides (see protein data bank entry 4HW4).

While benzothiophene 7 and acetyl furan 5 were discovered independently using completely different lines of inquiry, the resemblance of key elements in the structures was uncanny. In the Mcl-1 bound conformation of 7, the distance between the carboxylate carbon and the center of the chlorodimethylphenoxy substituent was 8.4 Å. Applicants could dock compound 5 into the same space occupied on Mcl-1 by 7 without unfavorable steric interactions (using AutoDock Vina).[18] In the docked conformation of 5, wherein the carbonyl oxygen was in closest proximity to R263, the distance between the carbonyl carbon and the center of the tolyl group was 8.3 Å. Applicants also observed that primary alcohol 8, derived from reducing carboxylic acid 7 with LiAlH₄, no longer had affinity for Mcl-1 measurable by ITC (FIG. 8B). This suggested that salt bridging was a critical aspect of the 7/Mcl-1 interaction and that giving 5 the ability to interact with the protein similarly may be advantageous. Based on the docking experiments above, Applicants chose to replace the methyl ketone in 5 with a carboxylic acid isostere—hoping to increase its affinity for Mcl-1 in the absence of membranes.

Applicants metalated pyrrolofuran 9[19] selectively at its 5' position with n-butyl lithium. Treatment of the lithiated species with ZnI₂ followed by tosylcyanide gave furanylnitrile 10 in 79% yield.[20]

Desilylation of 10 and derivatization with p-TsCl afforded 11 in high yield. To complete the target isostere, azide was cycloadded to the nitrile in 11 using diethylaluminum azide.[21] This provided furanyl tetrazole 12 after careful workup with a Na₂HPO₄/H₃PO₄ buffer solution (pH=2.1).[22] The overall yield of 12 from 9 was 33% (Scheme 1). A mixture of regioisomeric N-methyl tetrazoles 16, which are unable to ionize via proton transfer, were prepared as controls.[23]

Scheme 1.

Reagents and conditions: (a) "BuLi, THF, −78° C., 15 min; ZnI₂, 0° C., 3 min; TsCN, −78° C. to rt, 3 h, 79%; (b) TBAF, THF, rt, 10 min; (c) KHMDS, THF, 0° C., 15 min; TsCl, 0° C. to rt, 1 h, 90% (two steps); (d) Et₂AlN₃, PhMe, 85° C., 24 h; H₃O⁺, rt, 30 min, 62%; (e) 20 mol % Parkin's catalyst, H₂O, 100° C., 8 h, 83%; (f) NaH, MsCl, THF, 0° C. to rt, 3 h, 72%; or NaH, TsCl, THF, 0° C. to rt, 3 h, 80%; (g) K₂CO₃, MeI, MeCN/THF (1:1), 0° C. to rt, 5 h, 66%.

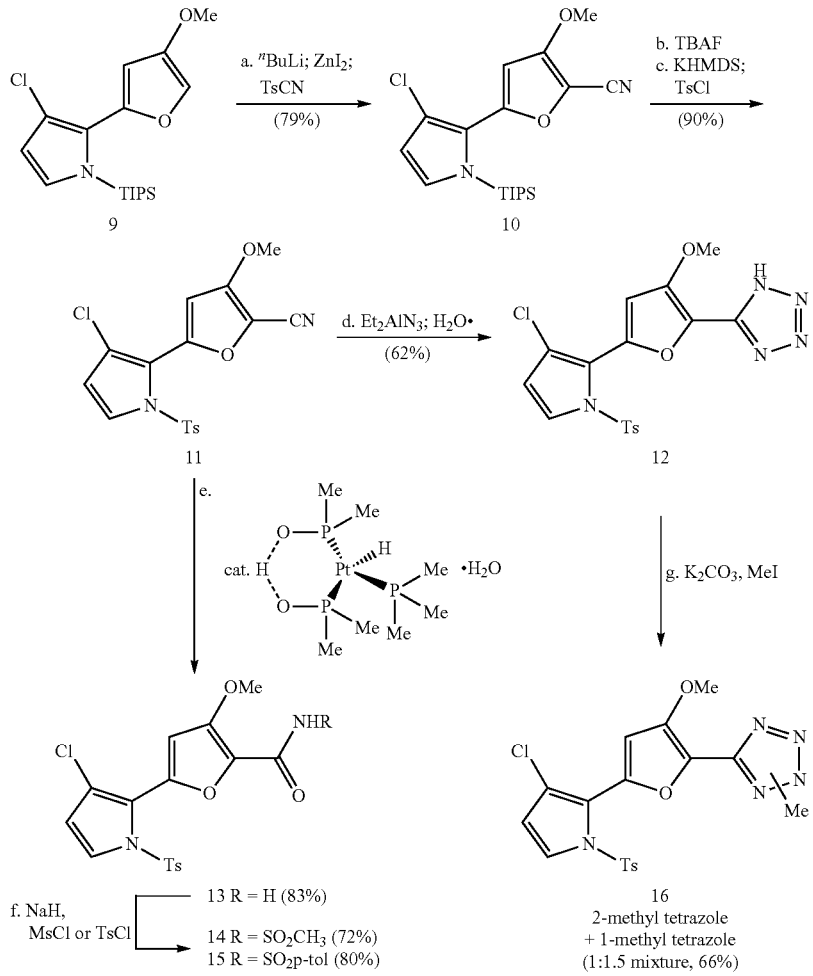

Figure 9A:
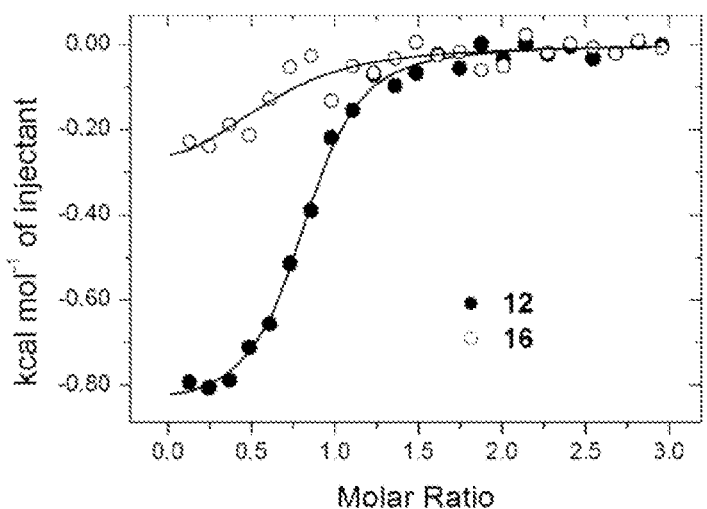
FIGS. 9A-9C. Compounds 12, 14 and 15 bind directly to recombinant Mcl-1 in vitro (FIGS. 9A and 9C) and stimulate Bak-mediated permeabilization of liposomal membranes (FIG. 8B). [$K_D$ (ITC) for 12, 14, and 15=0.7±0.12 μM, 3.4±0.49 μM, and 2.3 μM±0.16 μM, respectively].

Tetrazoles 12 and 16 were tested for specific binding to Mcl-1 using ITC. To Applicants' delight, compound 12 showed strong, saturable binding to the protein, whereas its N-methylated congeners 16 did not (FIG. 9A). Compound 12 bound Mcl-1 in an apparent 1:1 stoichiometry with $K_D$=0.7 µM. There was no indication of solubility differences in ITC buffer that would account for its improved performance relative to 5 and 16.

Figure 9B:
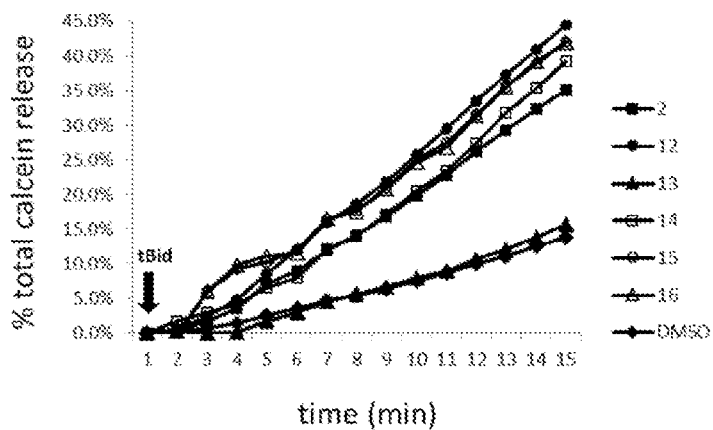
Figure 10:
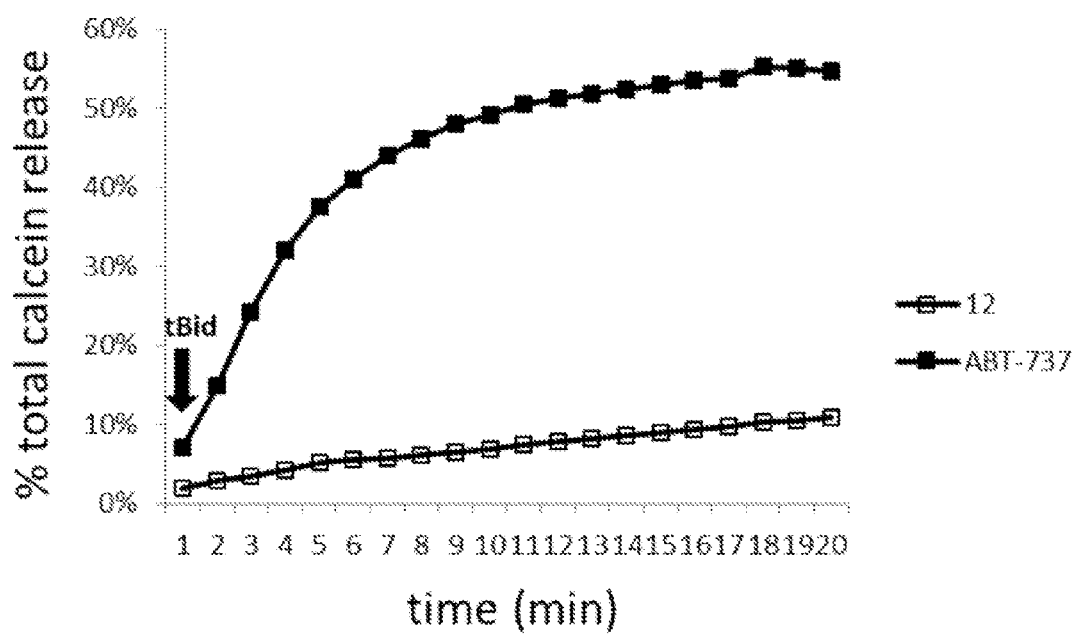
FIG. 10. Tetrazole 12 did not stimulate MOMP-like pore formations in liposomes that contain Bcl-xL in place of Mcl-1. ABT-737, a known antagonist of Bcl-xL, was used as a positive control. See reference 24 of Example; 2.

Compound 12 also successfully drove pore formations in the artificial membranes of Applicants' liposomal assay (FIG. 9B). Its activity exceeded that of 5 and obatoclax and was Mcl-1 dependent. Bak loaded proteoliposomes lacking Mcl-1 did not release calcein dye when treated with 12. Moreover, when Mcl-1 was replaced with Bcl-xL in the assay, 12 also had no effect (FIG. 10). This suggested a selectively for Mcl-1 over Bcl-xL which could be of value going forward. Toxic thrombocytopenia caused by ABT-737 in vivo has been correlated with Bcl-xL inhibition.[25]

Figure 8D:
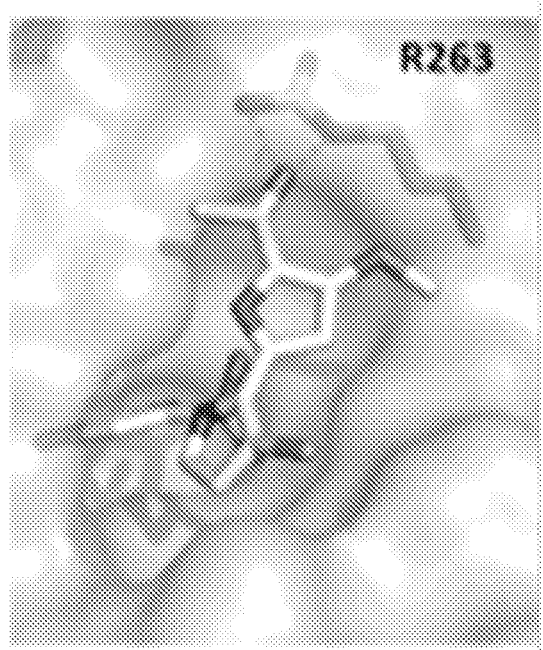
Figure 9C:
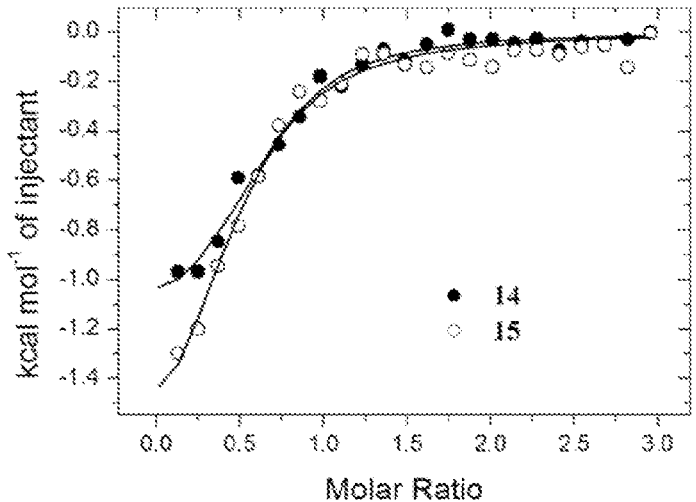

The discovery of Mcl-1 antagonist 5 and a rational means to convert that molecule into a prodginine-like structure (i.e. 12) having specific affinity for purified Mcl-1 holds considerable promise. Inhibition of anti-apoptotic Bcl-2 proteins by obatoclax is thought dependent on a supporting membrane environment. This could be true for 5 as well wherein its activity in liposomes (FIG. 6) may be driven by hydrophobic effects. In contrast, data for the 12/Mcl-1 interaction suggests a significant electrostatic component. Consistent with this idea, comparably performing Mcl-1 ligands could be generated using ionizable groups other than a tetrazole. Applicants synthesized N-acyl sulfonamides 14 and 15 via primary carboxamide 13 as outlined in Scheme 1.[26,27] Both 14 and 15 functioned in the liposomal assay and bound to recombinant Mcl-1 in vitro (FIG. 9C). While their affinity for the purified protein ($K_D$=3.4 and 2.3 μM respectively) was less than that for 12, these derivatives are amenable to further medicinal chemistry. Applicants are currently attempting to confirm hypothetical binding modes for 12 (FIG. 8D), 14 and/or 15 using X-ray co-crystallography.

References (Example 2)

[1]. Li, L.; et al., Science 2004, 305, 1471-1474; [2]. Wang, G.; et al., Nat. Chem. Bio. 2013, 9, 84-89; [3]. Petersen, S. L., et al., Cancer Cell 2007, 12, 445-456; [4]. Happo, L., et al., J. Cell Sci. 2012, 125, 1081-1087; [5]. Murthy, M. S. R, et al., U.S. Pat. No. 6,407,244 B1. Jun. 18, 2002; [6]. (a) Rahmani, M, et al., Clin. Cancer Res. 2008, 14, 8295-8301; [7]. Brumatti, G. & Ekert, P. G. Cell Death and Differentiation 2013, 20, 1440-1441; [8]. Fürstner, A. & Grabowski, E. J. ChemBioChem 2001, 2, 706-709; [9]. de Greñu, B. D., et al., Chem. Eur. J. 2011, 17, 14074-14083; [10]. Frederich, J. H. & Harran, P. G. J. Am. Chem. Soc. 2013, 135, 3788-3791; [11]. Ruffolo, S. C. & Shore, G. C. J. Biol. Chem. 2003, 278, 25039-25045; [12]. Stewart, M. L., et al., Nat. Chem. Biol. 2010, 6, 595-601; [13]. As a neat oil, pyrrolofuran 4 would degrade to a deep purple mixture of, as yet unidentified, products within hours at room temperature. Acetylation blocked this process. For details of the preparation see: Harran, P. G., et al., U.S. Provisional Patent Application No. 61/947,211. Filed Mar. 3, 2014; [14]. Nguyen, M., et al., PNAS 2007, 104, 19512-19517; [15]. Wang, Y. & Tjandra, N. J. Biol. Chem. 2013, 288, 35840-35851; [16]. Friberg, A., et al., J. Med. Chem. 2013, 56, 15-30; [17]. Shuker, S. B., et al., Science, 1996, 274, 1531-1534; [18]. Trott, O.; Olson, A. J. J. Comp. Chem. 2010, 31, 455-461; [19]. Frederich, J. H., et al., Tet. Lett. 2013, 54, 2645-2647; [20]. Nagasaki, I., et al., Heterocycles 1997, 46, 443-450; [21]. Et2AlN3 was generated from Et2AlCl and NaN3 on small scales (<1 g) and used immediately; [22]. Huff, B. E. & Staszak, M. A. Tet. Lett. 1993, 34, 8011-8014; [23]. Vieira, E., et al., J. Bioorg. Med. Chem. Lett. 2005, 15, 4628-4631; [24]. Oltersdorf, T., et al., Nature 2005, 435, 677-681; [25]. Vandenberg, C. J. & Cory, S. Blood 2013, 121, 2285-2288; [26]. For reference, approximate pKa values: thiophene 2-carboxylic acids=3.5, 5-aryl tetrazoles=4.3, N-acyl sulfonamides=2.5; [27]. Parkins, A. W. Platinum Metals Rev. 1996, 40, 169-174.

EMBODIMENTS

Embodiments disclosed herein include the following:

Embodiment 1

A compound having the formula:

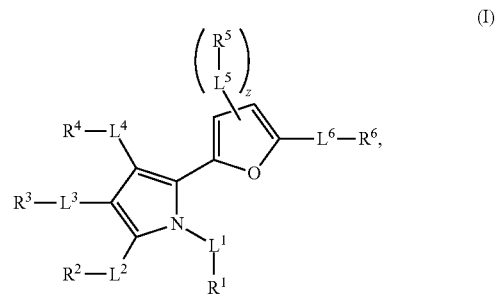

(I)

wherein, $L^1$, $L^2$, $L^3$, $L^4$, $L^5$, and $L^6$ are independently a bond, —C(O)—, —C(O)O—, —C(O)NR$^7$—, —O—, —S(O)$_n$—, —S(O)NR$^7$—, —C(O)NR$^7$S(O)$_2$—, —NR$^7$—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_2$Ph, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n is 0, 1, or 2; $R^1$ is hydrogen, halogen, —N$_3$, —CF$_3$, —CCl$_3$, —CBr$_3$, —CI$_3$, —CN, —CHO, =O, —OR$^{1A}$, —NR$^{1B}$R$^{1C}$, —COOR$^{1A}$, —CONR$^{1B}$R$^{1C}$, —NO$_2$, —SR$^{1D}$, —SO$_{n1}$OR$^{1B}$, —S(O)$_{n1}$OR$^{1B}$, —S(O)$_{n1}$NR$^{1B}$R$^{1C}$, —NHNR$^{1B}$R$^{1C}$, —ONR$^{1B}$R$^{1C}$, —NHC(O)NHNR$^{1B}$R$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^1$ and $R^2$ are optionally joined together to form a substituted or unsubstituted cycloalkyl, substituted or unsubstituted heterocycloalkyl, substituted or unsubstituted aryl, or substituted or unsubstituted heteroaryl; $R^2$ is hydrogen, halogen, —N$_3$, —CF$_3$, —CCl$_3$, —CBr$_3$, —CI$_3$, —CN, —CHO, =O, —OR$^{2A}$, —NR$^{2B}$R$^{2C}$, —COOR$^{2A}$, —CONR$^{2B}$R$^2$, NO$_2$, SR$^{2D}$, —SO$_{n2}$R$^{2B}$, —SO$_{n2}$OR$^{2B}$, —SO$_{n2}$NR$^{2B}$R$^2$, —NHNR$^{2B}$R$^{2C}$, —ONR$^{2B}$R$^{2C}$, —NHC(O)NHNR$^{2B}$R$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^2$ and $R^3$ are optionally joined together to form a substituted or unsubstituted cycloalkyl, substituted or unsubstituted heterocycloalkyl, substituted or unsubstituted aryl, or substituted or unsubstituted heteroaryl; $R^3$ is hydrogen, halogen, —N$_3$, —CF$_3$, —CCl$_3$, —CBr$_3$, —CI$_3$, —CN, —CHO, =O, —OR$^{3A}$, —NR$^{3B}$R$^{3C}$, —COOR$^{3A}$, —CONR$^{3B}$R$^{3C}$, NO$_2$, SR$^{3D}$, —SO$_{n3}$R$^{3B}$, —SO$_{n3}$OR$^{3B}$, —SO$_{n3}$NR$^{3B}$R$^{3C}$, —NHNR$^{3B}$R$^{3C}$, —ONR$^{3B}$R$^{3C}$, —NHC (O)NHNR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^3$ and R$^4$ are optionally joined together to form a substituted or unsubstituted cycloalkyl, substituted or unsubstituted heterocycloalkyl, substituted or unsubstituted aryl, or substituted or unsubstituted heteroaryl; R$^4$ is hydrogen, halogen, —N$_3$, —CF$_3$, —CCl$_3$, —CBr$_3$, —CI$_3$, —CN, —CHO, =O, —OR$^{4A}$, —NR$^{4B}$R$^{4C}$, —COOR$^{4A}$, —CONR$^{4B}$R$^{4C}$, NO$_2$, SR$^{4D}$, —SO$_{n4}$R$^{4B}$, —SO$_{n4}$OR$^{4B}$, —SO$_{n4}$NR$^{4B}$R$^{4C}$, —NHNR$^{4B}$R$^{4C}$, —ONR$^{4B}$R$^{4C}$, —NHC(O)NHNR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^5$ is independently hydrogen, halogen, —N$_3$, —CF$_3$, —CCl$_3$, —CBr$_3$, —CI$_3$, —CN, —CHO, =O, —OR$^{5A}$, —NR$^{5B}$R$^{5C}$, —COOR$^{5A}$, —CONR$^{5B}$R$^{5C}$, NO$_2$, SR$^{5D}$, —SO$_{n5}$R$^{5B}$, —SO$_{n5}$OR$^{5B}$, —SO$_{n5}$NR$^{5B}$R$^{5C}$, —NHNR$^{5B}$R$^{5C}$, —ONR$^{5B}$R$^{5C}$, —NHC(O)NHNR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^5$ and R$^6$ are optionally joined together to form a substituted or unsubstituted cycloalkyl, substituted or unsubstituted heterocycloalkyl, substituted or unsubstituted aryl, or substituted or unsubstituted heteroaryl; R$^6$ is hydrogen, halogen, —N$_3$, —CF$_3$, —CCl$_3$, —CBr$_3$, —CI$_3$, —CN, —CHO, =O, —OR$^{6A}$, —NR$^{6B}$R$^{6C}$, —COOR$^{6A}$, —CONR$^{6B}$R$^{6C}$, NO$_2$, SR$^{6D}$, —SO$_{16}$R$^{6B}$, —SO$_{n6}$OR$^{6B}$, —SO$_{n6}$NR$^{6B}$R$^{6C}$, —NHNR$^{6B}$R$^6$, —ONR$^{6B}$R$^6$, —NHC(O)NHNR$^{6B}$R$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$, R$^{2A}$, R$^{3A}$, R$^{4A}$, R$^{5A}$, R$^{6A}$, R$^{1B}$, R$^{2B}$, R$^{3B}$, R$^{4B}$, R$^{5B}$, R$^{6B}$, R$^{1C}$, R$^{2C}$, R$^{3C}$, R$^{4C}$, R$^{5C}$, R$^{6C}$, R$^{1D}$, R$^{2D}$, R$^{3D}$, R$^{4D}$, R$^{5D}$, and R$^{6D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^{6B}$ and R$^{6C}$, are optionally joined together to form a substituted or unsubstituted cycloalkyl, substituted or unsubstituted heterocycloalkyl, substituted or unsubstituted aryl, or substituted or unsubstituted heteroaryl; n1, n2, n3, n4, n5, and n6 are independently 1 or 2; and z is 1 or 2.

Embodiment 2

The compound of embodiment 1 wherein L$^1$ is a bond, —S(O)$_2$—, or substituted or unsubstituted alkylene.

Embodiment 3

The compound of any one of embodiments 1 to 2, wherein L$^1$ is a bond, or —S(O)$_2$—.

Embodiment 4

The compound of any one of embodiments 1 to 3, wherein L$^2$ and L$^3$ are independently a bond or substituted or unsubstituted alkylene.

Embodiment 5

The compound of any one of embodiments 1 to 4, wherein L$^2$ and L$^3$ are a bond.

Embodiment 6

The compound of any one of embodiments 1 to 5, wherein L$^4$ is a bond, S(O)$_2$—, or substituted or unsubstituted alkylene.

Embodiment 7

The compound of any one of embodiments 1 to 6, wherein L$^4$ is a bond or S(O)$_2$—.

Embodiment 8

The compound of any one of embodiments 1 to 7, wherein L$^5$ is a bond, —O—, or substituted or unsubstituted alkylene.

Embodiment 9

The compound of any one of embodiments 1 to 8, wherein L$^5$ is a bond or —O—.

Embodiment 10

The compound of any one of embodiments 1 to 9, wherein L$^6$ is a bond, —C(O)—, —C(O)NR$^7$, —S(O)$_2$—, or substituted or unsubstituted alkylene.

Embodiment 11

The compound of any one of embodiments 1 to 10, wherein L$^6$ is a bond or —C(O)—.

Embodiment 12

The compound of any one of embodiments 1 to 11 having the formula:

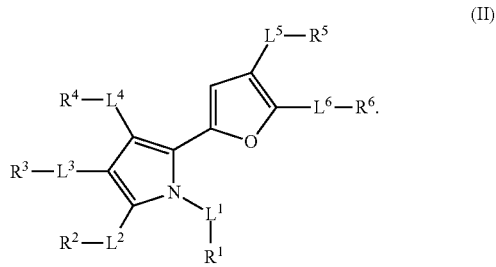

(II)

Embodiment 13

The compound of any one of embodiments 1 to 12, wherein R$^4$ is halogen, substituted or substituted alkyl, substituted or unsubstituted heteroalkyl, substituted or unsubstituted aryl or joined together with R$^3$ to form a substituted or unsubstituted cycloalkyl, substituted or unsubstituted heterocycloalkyl, or substituted or unsubstituted aryl.

Embodiment 14

The compound of any one of embodiments 1 to 13, wherein $R^4$ is halogen.

Embodiment 15

The compound of any one of embodiments 1 to 13, wherein $R^4$ is $R^{11}$-substituted or unsubstituted alkyl.

Embodiment 16

The compound of embodiment 15, wherein $R^{11}$ is halogen, oxo, —OH, substituted or unsubstituted alkyl or substituted or unsubstituted aryl.

Embodiment 17

The compound of any one of embodiments 1 to 13, wherein $R^4$ is $R^{11}$-substituted or unsubstituted aryl.

Embodiment 18

The compound of any one of embodiments 1 to 13, wherein $R^4$ and $R^3$ to form a substituted or unsubstituted cycloalkyl, substituted or unsubstituted heterocycloalkyl, or substituted or unsubstituted aryl.

Embodiment 19

The compound of any one of embodiments 1 to 18, wherein $R^2$ is hydrogen, joined together with $R^1$ to form a substituted or unsubstituted cycloalkyl or substituted or unsubstituted heterocycloalkyl, or joined together with $R^3$ to form substituted or unsubstituted heterocycloalkyl or substituted or unsubstituted aryl.

Embodiment 20

The compound of any one of embodiments 1 to 19, wherein $R^2$ is hydrogen.

Embodiment 21

The compound of any one of embodiments 1 to 19, wherein $R^2$ is joined together with $R^3$ to form a substituted or unsubstituted aryl.

Embodiment 22

The compound of any one of embodiments 1 to 19, wherein $R^2$ is joined together with $R^1$ to form a substituted or unsubstituted heterocycloalkyl.

Embodiment 23

The compound of any one of embodiments 1 to 22, wherein $R^3$ is hydrogen.

Embodiment 24

The compound of any one of embodiments 1 to 23 having the formula:

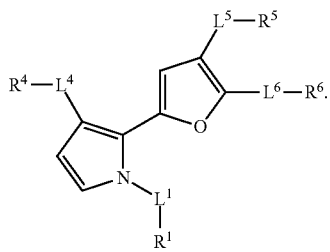

(III)

Embodiment 25

The compound of any one of embodiments 1 to 24, wherein $R^5$ is —$OR^{5A}$, $CF_3$, substituted or unsubstituted alkyl, substituted or unsubstituted aryl, substituted or unsubstituted heteroaryl.

Embodiment 26

The compound of any one of embodiments 1 to 25, wherein $R^5$ is —$OR^{5A}$, wherein $R^{5A}$ is $R^{13}$-substituted or unsubstituted alkyl, $R^{13}$-substituted or unsubstituted heteroalkyl; $R^{13}$ is halogen —OH, =O, $CF_3$, —$NR^{13A}R^{13B}$, substituted or unsubstituted alkyl, substituted or unsubstituted aryl, or substituted or unsubstituted heteroaryl; $R^{13A}$ and $R^{13B}$ are independently hydrogen or substituted or unsubstituted alkyl.

Embodiment 27

The compound of any one of embodiments 1 to 24, wherein $R^5$ is joined together with $R^6$ to form a substituted or unsubstituted heterocycloalkyl or substituted or unsubstituted heteroaryl.

Embodiment 28

The compound of any one of embodiments 1 to 27, wherein $R^6$ is halogen, —CN, substituted or unsubstituted alkyl, substituted or unsubstituted heterocycloalkyl, substituted or unsubstituted aryl, substituted or unsubstituted heteroaryl.

Embodiment 29

The compound of any one of embodiments 1 to 28, wherein $R^6$ is $R^{16}$-substituted or unsubstituted alkyl, wherein $R^{16}$ is $NR^{16a}R^{16b}$, $R^{17}$-substituted or unsubstituted heterocycloalkyl, $R^{17}$-substituted or unsubstituted aryl; $R^{16a}$ and $R^{16b}$ are independently substituted or unsubstituted alkyl, joined together to form a heterocycloalkyl; $R^{17}$ is halogen, —$N_3$, —$NO_2$, —$CF_3$, —$CCl_3$, —$CBr_3$, —$CI_3$, —CN, —OH, =O, —$NH_2$, —COOH, —$CONH_2$, —SH, —$SO_3H$, —$SO_4H$, —$SO_2NH_2$, —$NHNH_2$, —$ONH_2$, —$OCH_3$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 30

The compound of any one of embodiments 1 to 29, wherein $R^1$ is substituted or unsubstituted alkyl, substituted or unsubstituted hetercycloalkyl, substituted or unsubstituted aryl, substituted or unsubstituted heteroaryl, or wherein $R^1$ and $R^2$ are joined together to form a substituted or unsubstituted heterocycloalkyl.

Embodiment 31

The compound of any one of embodiments 1 to 29, wherein $R^1$ and $R^2$ are joined together to form a substituted or unsubstituted cycloalkyl, substituted or unsubstituted hetercycloalkyl, substituted or unsubstituted aryl or substituted or unsubstituted heteroaryl.

Embodiment 32

The compound of any one of embodiments 1 to 29, wherein $R^2$ and $R^3$ are joined together to form a substituted or unsubstituted cycloalkyl, substituted or unsubstituted hetercycloalkyl, substituted or unsubstituted aryl or substituted or unsubstituted heteroaryl.

Embodiment 33

The compound of any one of embodiments 1 to 29, wherein $R^3$ and $R^4$ are joined together to form a substituted or unsubstituted cycloalkyl, substituted or unsubstituted hetercycloalkyl, substituted or unsubstituted aryl or substituted or unsubstituted heteroaryl.

Embodiment 34

The compound of any one of embodiments 1 to 33, wherein $R^1$ is substituted or unsubstituted alkyl.

Embodiment 35

The compound of any one of embodiments 1 to 33, wherein $R^1$ is substituted or unsubstituted $C_1$-$C_{10}$ alkyl.

Embodiment 36

The compound of any one of embodiments 1 to 35, wherein $R^1$ is substituted or unsubstituted $C_1$-$C_5$ alkyl.

Embodiment 37

The compound of any one of embodiments 1 to 34, wherein $R^1$ is $R^9$-substituted $C_2$ alkyl and $R^9$ is methyl.

Embodiment 38

The compound of any one of embodiments 1 to 34, wherein $R^1$ is substituted or unsubstituted aryl or substituted or unsubstituted heteroaryl.

Embodiment 39

The compound of any one of embodiments 1 to 34, wherein $R^1$ is substituted or unsubstituted 5-8 membered aryl or substituted or unsubstituted 5-8 membered heteroaryl.

Embodiment 40

The compound of any one of embodiments to 38, wherein $R^1$ and $R^2$ are joined together to form an R-substituted or unsubstituted heterocycloalkyl, wherein R is substituted or unsubstituted alkyl or —S(O)$_2$.

Embodiment 41

The compound of embodiment 1 having the formula:

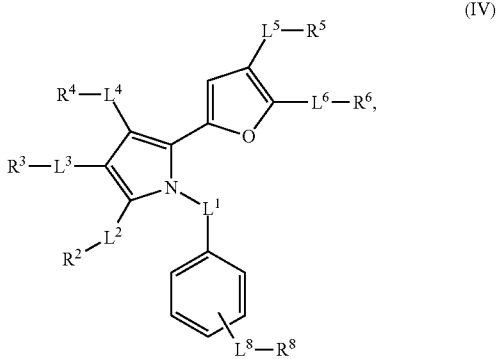

(IV)

wherein, $L^8$ is independently a bond, —C(O)—, —C(O)O—, —OC(O)—, —C(O)NR$^7$—, —NR$^7$C(O)—, —O—, —S(O)$_n$—, —S(O)NR$^7$—, —C(O)NR$^7$S(O)$_2$—, —NR$^7$—, OR$^7$OP(O)—, NR$^7$S(O)$_2$—, —(NR$^7$)NP(O)—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^8$ is independently hydrogen, halogen, —N$_3$, —CF$_3$, —CCl$_3$, —CBr$_3$, —CI$_3$, —CN, —CHO, =O, —OR$^{8A}$, —NR$^{8B}$R$^{8C}$, —COOR$^{8A}$, —CONR$^{8B}$R$^{8C}$, NO$_2$, SR$^{8D}$, —SO$_{n8}$R$^{8B}$, —SO$_{n8}$OR$^{8B}$, —SO$_{n8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{8A}$, $R^{8B}$, $R^{8C}$, and $R^{8D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n8 is 1, 2, 3, 4, or 5.

Embodiment 42

The compound of embodiment 41, wherein $L^1$ is a bond, —S(O)$_2$—, or substituted or unsubstituted $C_1$-$C_5$ alkylene.

Embodiment 43

The compound of any one of embodiments 41-42, wherein $L^8$ is a bond or substituted or unsubstituted $C_1$-$C_5$ alkylene.

Embodiment 44

The compound of any one of embodiments 4143, wherein $R^8$ is hydrogen, halogen or substituted or unsubstituted $C_1$-$C_5$ alkyl.

Embodiment 45

The compound of any one of embodiments 41-44, wherein $R^8$ is methyl.

Embodiment 46

The compound of any one of embodiments 41-45, wherein $L^2$ and $L^3$ are independently a bond, or substituted or unsubstituted $C_1$-$C_5$ alkylene.

Embodiment 47

The compound of any one of embodiments 41-46, wherein $R^2$ and $R^3$ are independently hydogen or are joined together to form a substituted or unsubstituted cycloalkyl, substituted or unsubstituted hetercycloalkyl, substituted or unsubstituted aryl or substituted or unsubstituted heteroaryl.

Embodiment 48

The compound of any one of embodiments 41-47 wherein $R^2$ and $R^3$ are joined together to form an unsubstituted aryl.

Embodiment 49

The compound of any one of embodiments 41-48, wherein $R^2$ and $R^3$ are joined together to form an unsubstituted phenyl.

Embodiment 50

The compound of any one of embodiments 41-49, wherein $L^4$ is a bond or substituted or unsubstituted $C_1$-$C_5$ alkylene.

Embodiment 51

The compound of any one of embodiments 41-50, wherein $R^4$ is hydrogen, halogen or substituted or unsubstituted $C_1$-$C_5$ alkyl.

Embodiment 52

The compound of any one of embodiments 41-51, wherein $R^4$ is —Cl or —Br.

Embodiment 53

The compound of any one of embodiments 41-52, wherein $L^5$ is a bond, —O—, substituted or unsubstituted $C_1$-$C_5$ alkylene or substituted or unsubstituted 1-5 membered heteroalkylene.

Embodiment 54

The compound of any one of embodiments 41-53, wherein $R^5$ is hydrogen or substituted or unsubstituted $C_1$-$C_5$ alkyl.

Embodiment 55

The compound of any one of embodiments 41-54, wherein $R^5$ is unsubstituted $C_1$-$C_5$ alkyl.

Embodiment 56

The compound of any one of embodiments 41-55, wherein $R^5$ is methyl.

Embodiment 57

The compound of any one of embodiments 41-54, wherein $R^5$ is substituted $C_1$-$C_5$ alkyl.

Embodiment 58

The compound of any one of embodiments 41-54 or 57, wherein $R^5$ is $R^{13}$-substituted $C_1$-$C_3$ alkyl and $R^{13}$ is substituted or unsubstituted 6 membered heterocycloalkyl or substituted or unsubstituted 6 membered heteroaryl.

Embodiment 59

The compound of any one of embodiments 41-54 or 57-58, wherein $R^5$ is $R^{13}$-substituted $C_1$-$C_3$ alkyl and $R^{13}$ is unsubstituted morpholinyl or unsubstituted pyridinyl.

Embodiment 60

The compound of any one of embodiments 41-59, wherein $L^6$ is a bond, —C(O)—, —C(O)O—, —C(O)NR$^7$S(O)$_2$—, or substituted or unsubstituted $C_1$-$C_5$ alkylene.

Embodiment 61

The compound of embodiment 60, wherein $R^6$ is —C(O)OR$^{6A}$, substituted or unsubstituted $C_1$-$C_5$ alkyl, substituted or unsubstituted $C_1$-$C_5$ heteroalkyl, substituted or unsubstituted aryl, or substituted or unsubstituted heteroaryl.

Embodiment 62

The compound of any one of embodiments 60-61, wherein $R^6$ is —C(O)OR$^{6A}$ and $R^{6A}$ is hydrogen.

Embodiment 63

The compound of any one of embodiments 60-61, wherein $R^6$ is unsubstituted $C_1$-$C_3$ alkyl.

Embodiment 64

The compound of any one of embodiments 60-61 and 63, wherein $R^6$ is methyl.

Embodiment 65

The compound of any one of embodiments 60-61, wherein $R^6$ is substituted or unsubstituted $C_1$-$C_3$ alkyl.

Embodiment 66

The compound of any one of embodiments 60-61 and 65, wherein $R^6$ is $R^{16}$-substituted or unsubstituted $C_3$ alkyl and $R^{16}$ is substituted or unsubstituted 6 membered heterocycloalkyl.

Embodiment 67

The compound of any one of embodiments 60-61 and 65, wherein $R^6$ is $R^{16}$-substituted or unsubstituted $C_1$ alkyl and $R^{16}$ is substituted or unsubstituted aryl.

Embodiment 68

The compound of any one of embodiments 60-61 and 67, wherein $R^6$ is $R^{16}$-substituted $C_1$ alkyl, $R^{16}$ is $R^{17}$-substituted or unsubstituted phenyl and $R^{17}$ is —$NH_2$.

Embodiment 69

The compound of any one of embodiments 60-61, wherein $R^6$ is $R^{16}$-substituted or unsubstituted $C_1$ alkyl and $R^{16}$ is substituted or unsubstituted 6 membered heteroaryl.

Embodiment 70

The compound of any one of embodiments 60-61 and 69, wherein $R^6$ is $R^{16}$-substituted $C_1$ alkyl and $R^{16}$ is unsubstituted pyridinyl.

Embodiment 71

The compound of any one of embodiments 60-61, wherein $R^6$ is $R^{16}$-substituted $C_1$-$C_3$ heteroalkyl and $R^{16}$ is —O or —OH.

Embodiment 72

The compound of any one of embodiments 60-61, wherein $R^6$ is substituted or unsubstituted 5-8 membered aryl.

Embodiment 73

The compound of any one of embodiments 60-61 or 72, wherein $R^6$ is $R^{16}$-substituted or unsubstituted 5-6 membered aryl and $R^{16}$ is hydrogen, halogen, =O, —OH, or substituted or unsubstituted $C_1$-$C_5$ alkyl.

Embodiment 74

The compound of any one of embodiments 60-61 or 72-73, wherein $R^6$ is $R^{16}$-substituted or unsubstituted phenyl and $R^{16}$ is hydrogen, —OH, halogen or unsubstituted $C_1$-$C_3$ alkyl.

Embodiment 75

The compound of any one of embodiments 60-61 or 72-73, wherein $R^6$ is $R^{16}$-substituted or unsubstituted cyclopentadienyl and $R^{16}$ is —O or —OH.

Embodiment 76

The compound of any one of embodiments 60-61, wherein $R^6$ is substituted or unsubstituted 5-8 membered heteroaryl.

Embodiment 77

The compound of any one of embodiments 60-61 or 76, wherein $R^6$ is unsubstituted triazolyl, tetrazolyl, pyrrolyl, pyrridinyl or oxodiazolyl.

Embodiment 78

The compound of any one of embodiments 60-61 or 76, wherein $R^6$ is $R^{16}$-substituted 5-8 membered heteroaryl, $R^{16}$ is $R^{17}$-substituted or unsubstituted 5 membered heteroalkyl and $R^{17}$ is =O or methyl.

Embodiment 79

The compound of any one of embodiments 60-61 or 76, wherein $R^6$ is $R^{16}$-substituted 5-8 membered heteroaryl, $R^{16}$ is $R^{17}$-substituted or unsubstituted $C_1$-$C_3$ alkyl and $R^{17}$ is unsubstituted morpholinyl.

Embodiment 80

The compound of any one of embodiments 60-61 or 76, wherein $R^6$ is $R^{16}$-substituted 5-8 membered heteroaryl and $R^{16}$ is unsubstituted $C_1$-$C_3$ alkyl.

Embodiment 81

The compound of any one of embodiments 60-61 or 76-80, wherein $R^6$ is $R^{16}$-substituted triazolyl, tetrazolyl, pyrrolyl, pyrridinyl or oxodiazolyl.

Embodiment 82

The compound of embodiment 1 having the formula:

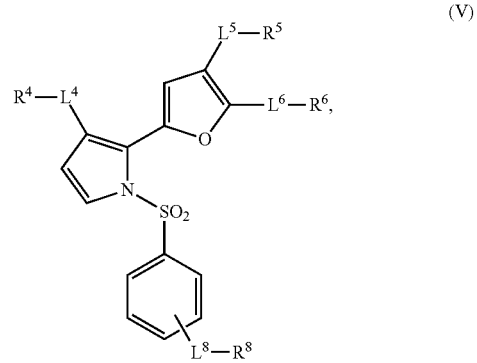

(V)

wherein, $L^8$ is independently a bond, —C(O)—, —C(O)O—, —OC(O)—, —C(O)NR$^7$—, —NR$^7$C(O)—, —O—, —S(O)$_n$—, —S(O)NR$^7$—, —C(O)NR$^7$S(O)$_2$—, —NR$^7$—, OR$^7$OP(O)—, NR$^7$S(O)$_2$—, —(NR$^7$)NP(O)—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^8$ is independently hydrogen, halogen, —N$_3$, —CF$_3$, —CCl$_3$, —CBr$_3$, —CI$_3$, —CN, —CHO, =O, —OR$^{8A}$, —NR$^{8B}$R$^{8C}$, —COOR$^{8A}$, —CONR$^{8B}$R$^{8C}$, NO$_2$, SR$^{8D}$, —SO$_{n8}$R$^{8B}$, —SO$_{n8}$OR$^{8B}$, —SO$_{n8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{8A}$, $R^{8B}$, $R^{8C}$, and $R^D$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n8 is 1, 2, 3, 4, or 5.

Embodiment 83

The compound of embodiment 41, wherein L⁸ is a bond or substituted or unsubstituted alkylene.

Embodiment 84

The compound of embodiment 41 or 83, wherein R⁸ is hydrogen, halogen, or substituted or unsubstituted alkyl.

Embodiment 85

A pharmaceutical composition comprising a compound of any one of embodiments 1 to 84 and a pharmaceutically acceptable excipient.

Embodiment 86

A method of treating cancer in a subject in need thereof, said method comprising administering an effective amount of a compound of any one of embodiments 1 to 85 to the subject.

Embodiment 87

The method of embodiment 86, wherein said cancer is leukemia.

Embodiment 88

A method of antagonizing Mcl-1, said method comprising contacting a Mcl-1 mixture with a compound of any one of embodiments 1 to 84.

What is claimed is:

1. A compound having the formula:

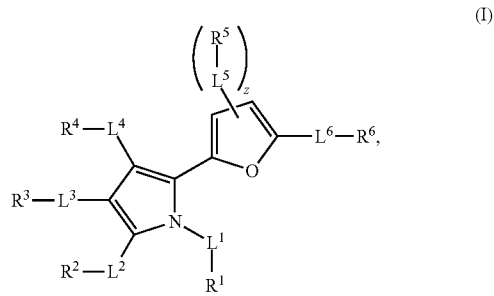

wherein, $L^1$, $L^2$, $L^3$, $L^4$, $L^5$, and $L^6$ are independently a bond, —C(O)—, —C(O)O—, —C(O)NR⁷—, —O—, —S(O)$_n$—, —S(O)NR⁷—, —C(O)NR⁷S(O)₂—, —NR⁷—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R⁷ is independently hydrogen, halogen, —N₃, —NO₂, —CF₃, —CCl₃, —CBr₃, —CI₃, —CN, —OH, —NH₂, —COOH, —CONH₂, —NO₂, —SH, —SO₂Cl, —SO₃H, —SO₂Ph, —SO₂NH₂, —NHNH₂, —ONH₂, —OCH₃, —NHCNHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n is 0, 1, or 2;

R¹ is halogen, —N₃, —CF₃, —CCl₃, —CBr₃, —CI₃, —CN, —CHO, =O, —OR¹ᴬ, —NR¹ᴮR¹ᶜ, —COOR¹ᴬ, —CONR¹ᴮR¹ᶜ, —NO₂, —SR¹ᴰ,

---

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: AMIDATION

<400> SEQUENCE: 1

Lys Ala Leu Glu Thr Leu Arg Arg Val Gly Asp Gly Val Gln Arg Asn
1               5                   10                  15

His Glu Thr Ala Phe
            20
```

—$SO_{n1}R^{1B}$, —$S(O)_{n1}OR^{1B}$, —$S(O)_{n1}NR^{1B}R^{1C}$, —$NHNR^{1B}R^{1C}$, —$ONR^{1B}R^{1C}$, —$NHC(O)NHNR^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^1$ and $R^2$ are optionally joined together to form a substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$N_3$, —$CF_3$, —$CCl_3$, —$CBr_3$, —$CI_3$, —CN, —CHO, =O, —$OR^{2A}$, —$NR^{2B}R^{2C}$, —$COOR^{2A}$, —$CONR^{2B}R^{2C}$, $NO_2$, $SR^{2D}$, —$SO_{n2}R^{2B}$, —$SO_{n2}OR^{2B}$, —$SO_{n2}NR^{2B}R^{2C}$, —$NHNR^{2B}R^{2C}$, —$ONR^{2B}R^{2C}$, —$NHC(O)NHNR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^2$ and $R^3$ are optionally joined together to form a substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$N_3$, —$CF_3$, —$CCl_3$, —$CBr_3$, —$CI_3$, —CN, —CHO, =O, —$OR^{3A}$, —$NR^{3B}R^{3C}$, —$COOR^{3A}$, —$CONR^{3B}R^{3C}$, $NO_2$, $SR^{3D}$, —$SO_{n3}R^{3B}$, —$SO_{n3}OR^{3B}$, —$SO_{n3}NR^{3B}R^{3C}$, —$NHNR^{3B}R^{3C}$, —$ONR^{3B}R^{3C}$, —$NHC(O)NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^3$ and $R^4$ are optionally joined together to form a substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$N_3$, —$CF_3$, —$CCl_3$, —$CBr_3$, —$CI_3$, —CN, —CHO, =O, —$OR^{4A}$, —$NR^{4B}R^{4C}$, —$COOR^{4A}$, —$CONR^{4B}R^{4C}$, $NO_2$, $SR^{4D}$, —$SO_{n4}R^{4B}$, —$SO_{n4}OR^{4B}$, —$SO_{n4}NR^{4B}R^{4C}$, —$NHNR^{4B}R^{4C}$, —$ONR^{4B}R^{4C}$, —$NHC(O)NHNR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently hydrogen, halogen, —$N_3$, —$CF_3$, —$CCl_3$, —$CBr_3$, —$CI_3$, —CN, —CHO, =O, —$OR^{5A}$, —$NR^{5B}R^{5C}$, —$COOR^{5A}$, —$CONR^{5B}R^{5C}$, $NO_2$, $SR^{5D}$, —$SO_{n5}R^{5B}$, —$SO_{n5}OR^{5B}$, —$SO_{n5}NR^{5B}R^{5C}$, —$NHNR^{5B}R^{5C}$, —$ONR^{5B}R^{5C}$, —$NHC(O)NHNR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^5$ and $R^6$ are optionally joined together to form a substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$N_3$, —$CF_3$, —$CCl_3$, —$CBr_3$, —$CI_3$, —CN, —CHO, =O, —$OR^{6A}$, —$NR^{6B}R^{6C}$, —$COOR^{6A}$, —$CONR^{6B}R^{6C}$, $NO_2$, $SR^{6D}$, —$SO_{n6}R^{6B}$, —$SO_{n6}OR^{6B}$, —$SO_{n6}NR^{6B}R^{6C}$, —$NHNR^{6B}R^{6C}$, —$ONR^{6B}R^{6C}$, —$NHC(O)NHNR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{2A}$, $R^{3A}$, $R^{4A}$, $R^{5A}$, $R^{6A}$, $R^{1B}$, $R^{2B}$, $R^{3B}$, $R^{4B}$, $R^{5B}$, $R^{6B}$, $R^{1C}$, $R^{2C}$, $R^{3C}$, $R^{4C}$, $R^{5C}$, $R^{6C}$, $R^{1D}R^{2D}$, $R^{3D}$, $R^{4D}$, $R^{5D}$, and $R^{6D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{6B}$ and $R^{6C}$, are optionally joined together to form a substituted or unsubstituted cycloalkyl, substituted or unsubstituted heterocycloalkyl, substituted or unsubstituted aryl, or substituted or unsubstituted heteroaryl;

n1, n2, n3, n4, n5, and n6 are independently 1 or 2; and z is 1 or 2.

2. The compound of claim 1, wherein $L^1$ is a bond, or —$S(O)_2$—.

3. The compound of claim 2, wherein $L^2$ and $L^3$ are independently a bond or substituted or unsubstituted alkylene.

4. The compound of claim 3, wherein $L^4$ is a bond or $S(O)_2$—.

5. The compound of claim 4, wherein $L^5$ is a bond, —O—, or substituted or unsubstituted alkylene.

6. The compound of claim 5, wherein $L^6$ is a bond or —C(O)—.

7. The compound of claim 6, wherein $R^4$ is halogen, substituted or unsubstituted alkyl, substituted or unsubstituted heteroalkyl, substituted or unsubstituted aryl or joined together with $R^3$ to form a substituted or unsubstituted cycloalkyl, substituted or unsubstituted heterocycloalkyl, or substituted or unsubstituted aryl.

8. The compound of claim 7, wherein $R^4$ is $R^{11}$-substituted or unsubstituted alkyl or $R^{11}$-substituted or unsubstituted aryl, wherein $R^{11}$ is halogen, oxo, —OH, substituted or unsubstituted alkyl or substituted or unsubstituted aryl.

9. The compound of claim 8, wherein $R^2$ is hydrogen, joined together with $R^1$ to form a substituted or unsubstituted cycloalkyl or substituted or unsubstituted heterocycloalkyl, or joined together with $R^3$ to form substituted or unsubstituted heterocycloalkyl or substituted or unsubstituted aryl.

10. The compound of claim 9, wherein $R^3$ is hydrogen.

11. The compound of claim 1 having the formula:

(III)

12. The compound of claim 11, wherein $R^5$ is —$OR^{5A}$, wherein $R^{5A}$ is $R^{13}$-substituted or unsubstituted alkyl, $R^{13}$-substituted or unsubstituted heteroalkyl;

$R^{13}$ is halogen —OH, =O, —CF$_3$, —NR$^{13A}$R$^{13B}$, substituted or unsubstituted alkyl, substituted or unsubstituted aryl, or substituted or unsubstituted heteroaryl;

$R^{13A}$ and $R^{13B}$ are independently hydrogen or substituted or unsubstituted alkyl.

13. The compound of claim 11, wherein $R^5$ is joined together with $R^6$ to form a substituted or unsubstituted heterocycloalkyl or substituted or unsubstituted heteroaryl.

14. The compound of claim 11, wherein $R^6$ is $R^{16}$-substituted or unsubstituted alkyl, wherein $R^{16}$ is —NR$^{16a}$R$^{16b}$, R$^{17}$-substituted or unsubstituted heterocycloalkyl, or R$^{17}$-substituted or unsubstituted aryl;

$R^{16a}$ and $R^{16b}$ are independently substituted or unsubstituted alkyl, joined together to form a heterocycloalkyl;

$R^{17}$ is halogen, —N$_3$, —NO$_2$, —CF$_3$, —CCl$_3$, —CBr$_3$, —CI$_3$, —CN, —OH, =O, —NH$_2$, —COOH, —CONH$_2$, —SH, —SO$_3$H, —SO$_4$H, —SO$_2$NH$_2$, —NHNH$_2$, —ONH$_2$, —OCH$_3$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

15. The compound of claim 14, wherein $R^1$ and $R^2$ are joined together to form a substituted or unsubstituted cycloalkyl, substituted or unsubstituted heterocycloalkyl, substituted or unsubstituted aryl or substituted or unsubstituted heteroaryl.

16. The compound of claim 15, wherein $R^1$ and $R^2$ are joined together to form an R-substituted or unsubstituted heterocycloalkyl, wherein R is substituted or unsubstituted alkyl or —S(O)$_2$.

17. The compound of claim 1 having the formula:

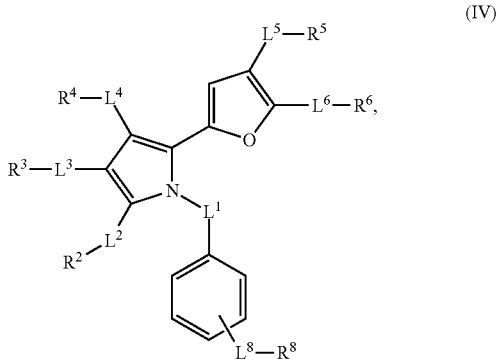

(IV)

wherein,

L$^8$ is independently a bond, —C(O)—, —C(O)O—, —OC(O)—, —C(O)NR$^7$—, —NR$^7$C(O)—, —O—, —S(O)NR$^7$—, —C(O)NR$^7$S(O)$_2$—, OR$^7$OP(O)—, NR$^7$S(O)$_2$—, —(NR$^7$)NP(O)—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^8$ is independently hydrogen, halogen, —N$_3$, —CF$_3$, —CCl$_3$, —CBr$_3$, —CI$_3$, —CN, —CHO, =O, —OR$^{8A}$, —NR$^{8B}$R$^{8C}$, —COOR$^{8A}$, —CONR$^{8B}$R$^{8C}$, NO$_2$, SR$^{8D}$, —SO$_{n8}$R$^{8B}$, —SO$_{n8}$OR$^{8B}$, —SO$_{n8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{8A}$, $R^{8B}$, $R^{8C}$, and $R^{8D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n8 is 1, 2, 3, 4, or 5.

18. The compound of claim 17, wherein $R^2$ and $R^3$ are independently hydogen or are joined together to form a substituted or unsubstituted cycloalkyl, substituted or unsubstituted heterocycloalkyl, substituted or unsubstituted aryl or substituted or unsubstituted heteroaryl.

19. The compound of claim 18, wherein $R^2$ and $R^3$ are joined together to form an unsubstituted phenyl.

20. The compound of claim 19, wherein $R^4$ is hydrogen, halogen or substituted or unsubstituted C$_1$-C$_5$ alkyl.

21. The compound of claim 20, wherein L$^5$ is a bond, —O—, substituted or unsubstituted C$_1$-C$_5$ alkylene or substituted or unsubstituted 1-5 membered heteroalkylene.

22. The compound of claim 21, wherein $R^5$ is unsubstituted C$_1$-C$_5$ alkyl.

23. The compound of claim 21, wherein $R^5$ is $R^{13}$-substituted C$_1$-C$_3$ alkyl and $R^{13}$ is substituted or unsubstituted 6 membered heterocycloalkyl or substituted or unsubstituted 6 membered heteroaryl.

24. The compound of claim 23, wherein $R^6$ is —C(O)OR$^{6A}$, substituted or unsubstituted C$_1$-C$_5$ alkyl, substituted or unsubstituted C$_1$-C$_5$ heteroalkyl, substituted or unsubstituted aryl, or substituted or unsubstituted heteroaryl.

25. The compound of claim 24, wherein $R^6$ is $R^{16}$-substituted or unsubstituted C$_3$ alkyl and $R^{16}$ is substituted or unsubstituted 6 membered heterocycloalkyl.

26. The compound of claim 24, wherein $R^6$ is $R^{16}$-substituted C$_1$ alkyl, $R^{16}$ is $R^{17}$-substituted or unsubstituted phenyl and $R^{17}$ is —NH$_2$.

27. The compound of claim 24, wherein $R^6$ is $R^{16}$-substituted C$_1$ alkyl and $R^{16}$ is unsubstituted pyridinyl.

28. The compound of claim 24, wherein $R^6$ is $R^{16}$-substituted C$_1$-C$_3$ heteroalkyl and $R^{16}$ is —O or —OH.

29. The compound of claim 24, wherein $R^6$ is $R^{16}$-substituted or unsubstituted 5-6 membered aryl and $R^{16}$ is hydrogen, halogen, =O, —OH, or substituted or unsubstituted C$_1$-C$_5$ alkyl.

30. The compound of claim 29, wherein $R^6$ is $R^{16}$-substituted or unsubstituted cyclopentadienyl and $R^{16}$ is —O or —OH.

31. The compound of claim 23, wherein $R^6$ is unsubstituted triazolyl, tetrazolyl, pyrrolyl, pyrridinyl or oxodiazolyl.

32. The compound of claim 30, wherein $R^6$ is $R^{16}$-substituted triazolyl, tetrazolyl, pyrrolyl, pyrridinyl or oxodiazolyl.

33. The compound of claim 1 having the formula:

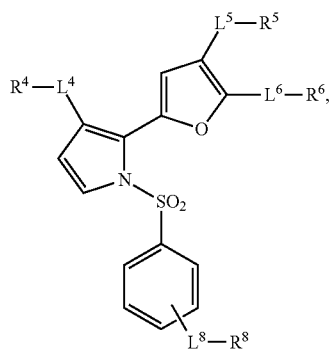
(V)

wherein,

L⁸ is independently a bond, —C(O)—, —C(O)O—, —OC(O)—, —C(O)NR⁷—, —NR⁷C(O)—, —O—, —S(O)$_n$—, —S(O)NR⁷—, —C(O)NR⁷S(O)$_2$—, OR⁷OP(O)—, NR⁷S(O)$_2$—, —(NR⁷)NP(O)—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R⁸ is independently hydrogen, halogen, —N₃, —CF₃, —CCl₃, —CBr₃, —CI₃, —CN, —CHO, =O, —OR$^{8A}$, —NR$^{8B}$R$^{8C}$, —COOR$^{8A}$, —CONR$^{8B}$R$^{8C}$, NO₂, SR$^{8D}$, —SO$_{n8}$R$^{8B}$, —SO$_{n8}$OR$^{8B}$, —SO$_{n8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{8A}$, R$^{8B}$, R$^{8C}$, and R$^{8D}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n8 is 1, 2, 3, 4, or 5.

34. A pharmaceutical composition comprising a compound of claim 1 and a pharmaceutically acceptable excipient.

* * * * *